United States Patent
Nakai et al.

(10) Patent No.: US 12,006,292 B2
(45) Date of Patent: Jun. 11, 2024

(54) PHOTORESPONSIVE COMPOUND

(71) Applicant: Konica Minolta, Inc., Tokyo (JP)

(72) Inventors: Yukiko Nakai, Toyohashi (JP); Kouji Sugama, Musashino (JP); Kazuaki Nakamura, Hino (JP); Toyoko Shibata, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 17/659,730

(22) Filed: Apr. 19, 2022

(65) Prior Publication Data

US 2023/0067136 A1 Mar. 2, 2023

(30) Foreign Application Priority Data

Apr. 30, 2021 (JP) ................... 2021-078059

(51) Int. Cl.
*C07D 231/12* (2006.01)
*C09J 7/25* (2018.01)
(Continued)

(52) U.S. Cl.
CPC .............. *C07D 231/12* (2013.01); *C09J 7/25* (2018.01); *G03G 9/08708* (2013.01);
(Continued)

(58) Field of Classification Search
None
See application file for complete search history.

(56) References Cited

U.S. PATENT DOCUMENTS

2004/0248025 A1* 12/2004 Miyakawa ......... G03G 15/0121
430/108.7
2013/0066068 A1 3/2013 Norikane et al.
(Continued)

FOREIGN PATENT DOCUMENTS

| JP | 2011-256155 A | 12/2011 | |
|----|---------------|---------|---|
| JP | 2011-256291 A | 12/2011 | |
| JP | 2020180177 A * | 11/2020 | ............ C08F 120/38 |

OTHER PUBLICATIONS

Claramunt et al., Synthesis and Mesogenic Properties of Schiff Bases Derived from Aminopyrazoles, 1999, Heterocylces, vol. 51, No. 4, 751-762.*

*Primary Examiner* — Eli D. Strah
(74) *Attorney, Agent, or Firm* — Lucas & Mercanti, LLP

(57) ABSTRACT

Provided is a compound that is fluidized by light irradiation and reversibly non-fluidized, is not significantly colored, and improves fixability and exhibits excellent image stability and color reproducibility when used for a toner.

Provided is a compound represented by the following general formula (1), which is fluidized by light irradiation and reversibly non-fluidized:

$$R_1-Z_1=Z_2-R_2 \quad \text{General Formula (1)}$$

wherein $Z_1$ and $Z_2$ are CH or N, and $Z_1 \neq Z_2$;

$R_1$ is an aromatic hydrocarbon group having a substituent $R_a$ selected from the group consisting of an alkyl group, an alkoxy group and a halogen atom at each of two ortho positions with respect to $Z_1$; and (Continued)

$R_2$ is a substituted or unsubstituted aromatic heterocyclic group.

14 Claims, 2 Drawing Sheets

(51) Int. Cl.
| | | |
|---|---|---|
| *G03G 9/087* | (2006.01) | |
| *G03G 15/20* | (2006.01) | |
| *B41J 11/00* | (2006.01) | |
| *C08F 212/08* | (2006.01) | |
| *C08F 220/18* | (2006.01) | |
| *C08F 257/02* | (2006.01) | |
| *C08F 285/00* | (2006.01) | |
| *G03G 9/09* | (2006.01) | |

(52) U.S. Cl.
CPC ..... *G03G 9/08728* (2013.01); *G03G 15/2064* (2013.01); *B41J 11/0021* (2021.01); *C08F 212/08* (2013.01); *C08F 220/1806* (2020.02); *C08F 257/02* (2013.01); *C08F 285/00* (2013.01); *G03G 9/0922* (2013.01)

(56) References Cited

U.S. PATENT DOCUMENTS

| | | | |
|---|---|---|---|
| 2018/0217518 A1* | 8/2018 | Takahashi | G03G 15/2007 |
| 2020/0264530 A1* | 8/2020 | Kusano | C09K 19/22 |
| 2022/0043333 A1* | 2/2022 | Nakai | G02F 1/0063 |
| 2022/0373913 A1* | 11/2022 | Sugama | G03G 15/657 |
| 2022/0390824 A1* | 12/2022 | Nakai | G03G 9/08722 |

* cited by examiner

PHOTORESPONSIVE COMPOUND

BACKGROUND

Technological Field

The present invention relates to a photoresponsive compound which is fluidized by light irradiation and reversibly non-fluidized.

Description of the Related Art

As a material whose fluidity is changed by light irradiation, a photoresponsive material is known. For example, an azobenzene compound (azobenzene derivative) disclosed in JP 2011-256155 A or JP 2011-256291 A undergoes a phase change in association with an isomerization reaction caused by light irradiation.

It is considered that an associated change in molecular structure induces a phase transition from a solid state to a fluid state. In addition, when the azobenzene compound is irradiated again with light at a different wavelength, heated, or left in a dark place at room temperature, a reverse reaction occurs and the compound is solidified again.

SUMMARY

However, the azobenzene derivatives disclosed in JP 2011-256155 A and JP 2011-256291 A are both colored yellow to orange, and have a problem that the azobenzene derivative does not enable reproduction of a desired color when applied to industrial products such as toners and adhesives. Further, according to studies made by the present inventors, it has been found that for the yellow to orange coloring, the color can be adjusted to a certain degree by changing a substituent of the azobenzene derivative, but it is impossible to attain a completely colorless or nearly colorless state.

Accordingly, an object of the present invention is to provide a compound that is fluidized by light irradiation and reversibly non-fluidized, is not significantly colored, and improves fixability and exhibits excellent image stability and color reproducibility when used for a toner.

To achieve at least one of the abovementioned objects, according to an aspect of the present invention, an azomethine compound having an aromatic hydrocarbon group and an aromatic heterocyclic group, respectively, at both ends of a C=N bond, in which the aromatic hydrocarbon group has specific substituents at two ortho positions with respect to C=N, is provided.

According to an aspect of the present invention, a compound represented by the following general formula (1), which is fluidized by light irradiation and reversibly non-fluidized, is provided:

[Chemical Formula 1]

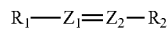

General Formula (1)

wherein
$Z_1$ and $Z_2$ are CH or N, and $Z_1 \neq Z_2$;
$R_1$ is an aromatic hydrocarbon group having a substituent $R_a$ selected from the group consisting of an alkyl group, an alkoxy group and a halogen atom at each of two ortho positions with respect to $Z_1$; and
$R_2$ is a substituted or unsubstituted aromatic heterocyclic group.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
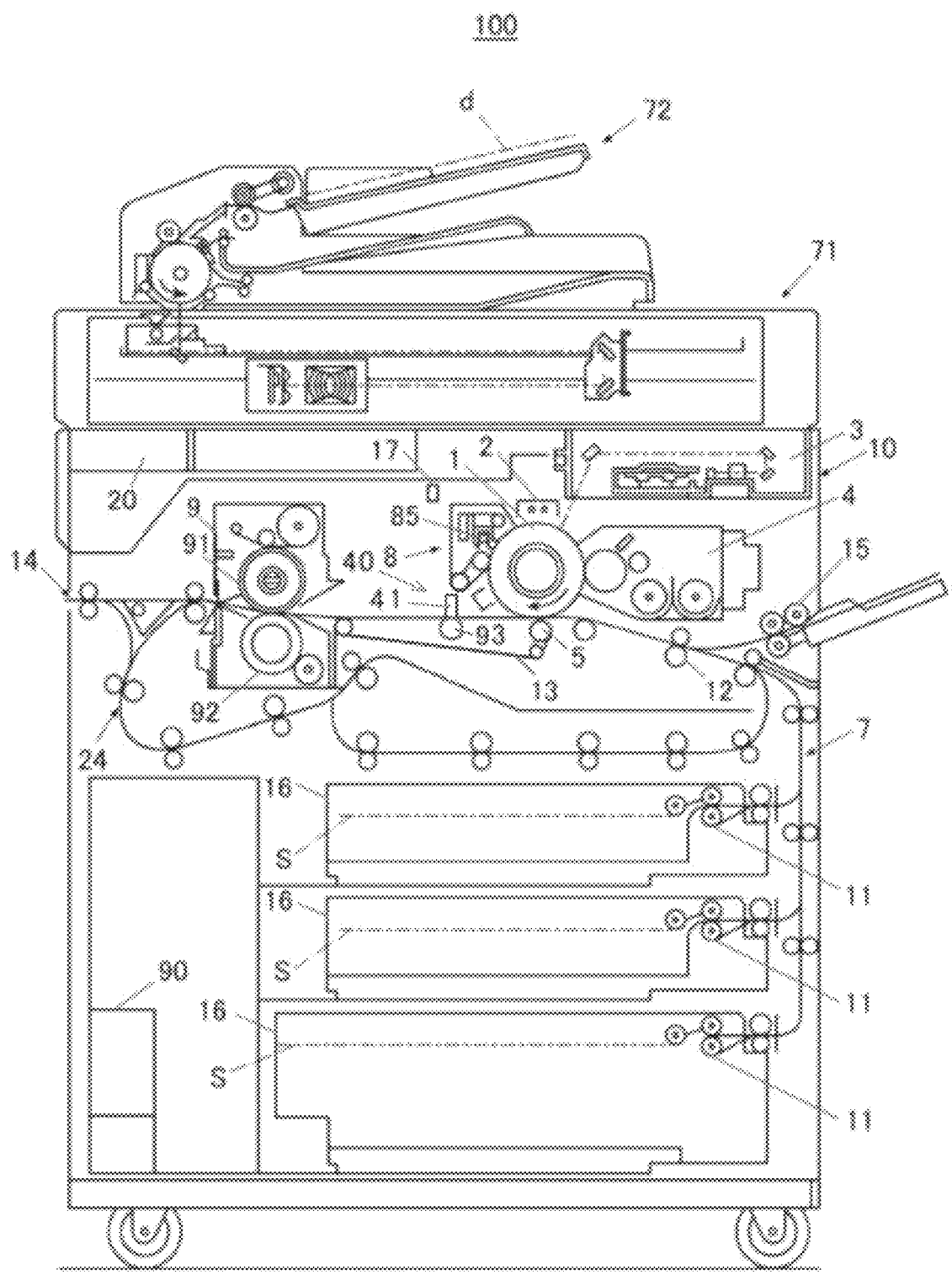
FIG. 1 is a schematic configuration diagram illustrating an image forming apparatus 100 used in an image forming method according to an embodiment of the present invention.

Hereinafter, one or more embodiments of the present invention will be described with reference to the drawings. However, the scope of the invention is not limited to the disclosed embodiments.

In the present specification, "X to Y" indicating a range means "X or more and Y or less". In addition, in the present specification, unless otherwise specified, operations and measurements of physical properties and the like are performed under conditions of room temperature (20° C. to 25° C.)/relative humidity of 40 to 50% RH.

<Photoresponsive Compound>

An embodiment of the present invention is a compound represented by the following general formula (1), which is fluidized by light irradiation and reversibly non-fluidized:

[Chemical Formula 2]

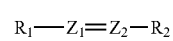

General Formula (1)

wherein
$Z_1$ and $Z_2$ are CH or N, and $Z_1 \neq Z_2$;
$R_1$ is an aromatic hydrocarbon group having a substituent $R_a$ selected from the group consisting of an alkyl group, an alkoxy group and a halogen atom at each of two ortho positions with respect to $Z_1$; and
$R_2$ is a substituted or unsubstituted aromatic heterocyclic group.

According to the present embodiment, it is possible to provide a compound that sufficiently secures a photoresponsive property of being fluidized by light irradiation and reversibly non-fluidized, and improves fixability and exhibits excellent image stability and good color reproducibility when used for a toner.

Here, the above general formula (1) is described using one of the following specific examples. As in the following formula, an aromatic hydrocarbon group $R_1$ such as a phenyl group is bonded to $Z_1$ (CH in the following formula), and an optionally substituted aromatic heterocyclic group $R_2$ is bonded to $Z_2$ (N in the following formula). In the present embodiment, the aromatic hydrocarbon group $R_1$ has a specific substituent $R_a$ (a $CH_3$ group in the following formula) on both two carbon atoms at an ortho position with respect to $Z_1$.

[Chemical Formula 3]

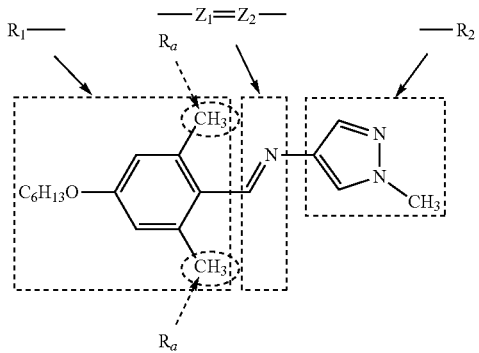

In the present specification, the compound of the present invention is also referred to as a "photoresponsive compound". With a predetermined structure as described above, it is possible to provide a compound that sufficiently secures a photoresponsive property of being fluidized by light irradiation and reversibly non-fluidized, and improves fixability and exhibits excellent image stability and good color reproducibility when used for a toner.

In the present specification, the phrase "fluidized by light irradiation and reversibly non-fluidized" refers to a phenomenon that the compound is turned from a non-fluid state to a fluid state by light irradiation and further returns to a non-fluid state. That is, at normal temperature and normal pressure, the compound of the present invention is in a non-fluid solid state when the compound is not irradiated with light, and the compound is softened and turned into a fluid state when irradiated with light. When the light irradiation is stopped, and the compound is left standing in a dark place at room temperature or under irradiation with visible light, or being heated, the compound returns to a non-fluid solid state. In the present specification, the fluid state refers to a state in which deformation occurs with a small external force.

A mechanism of exerting such a technical effect is presumed as follows. However, the technical scope of the present invention is not limited to such a mechanism. That is, the azobenzene compound is a material that absorbs light and softens (undergoes optical phase transition) from a solid state, and it is considered that the optical phase transition is caused by disorder of a crystal structure due to cis-trans isomerization. The azobenzene compound disclosed in JP 2011-256155 A or JP 2011-256291 A undergoes a phase change in association with an isomerization reaction caused by light irradiation, however, it has been found that since these compounds exhibit strong absorption due to n-π* transition in a visible light region, and are colored in orange, the compounds have a problem in that the compounds hardly allow a desired color to be reproduced when applied to industrial products.

In the present invention, a compound that is fluidized by light irradiation and reversibly non-fluidized and is not significantly colored has been provided by using a predetermined azomethine compound. By introduction of an azomethine moiety (C═N part) instead of the azobenzene moiety, the strong n-π* absorption in the azobenzene compound can be weakened, so that a compound that is not significantly colored can be realized.

In addition, in the compound that is reversibly fluidized and non-fluidized due to photoisomerization, it is considered that when a non-fluid trans isomer is irradiated with light and isomerized to a cis isomer, many trans isomers change to cis isomers, so that an ordered structure of the compound is disordered and a phase transition change, that is, a fluidization phenomenon can be induced. It is also considered that when the cis isomer returns to the trans isomer, an ordered structure is formed again, and a non-fluidization phenomenon can be induced. Therefore, in order to induce the phenomenon that the compound is fluidized, it is considered necessary that many trans isomers be isomerized to cis isomers. However, it is known that an azomethine compound generally has a higher rate of isomerization from a cis isomer to a trans isomer over an azobenzene compound, and it is expected that an azomethine compound having unsubstituted benzene rings introduced at both ends of a C═N bond is disadvantageous for inducing a phenomenon that the compound is reversibly fluidized and non-fluidized.

Thus, in the present invention, an azomethine compound, in which an aromatic hydrocarbon group and an aromatic heterocyclic group are present, respectively, at both ends of a C═N bond and a substituent $R_d$ selected from the group consisting of an alkyl group, an alkoxy group and a halogen atom is introduced at each of two ortho positions of the aromatic hydrocarbon group, enables efficient induction of fluidization associated with a photoisomerization reaction. This is considered to be because the presence of the specific substituent $R_a$ at each of two ortho positions of the aromatic hydrocarbon group stabilizes the cis isomer to generate a larger number of cis isomers as compared to a case where such a substituent is not present or such a substituent is present only at one ortho position.

Further, introduction of the compound of the present invention into a toner provides a toner that can be fixed by light irradiation, has excellent fixability and excellent image storability, and has high color reproducibility. By introducing the specific substituent $R_a$ at each of two ortho positions of the aromatic hydrocarbon group, the cis→trans reaction rate is reduced, and the cis isomer is stabilized to generate a larger number of cis isomers. It is considered that this induces fluidization, so that melting proceeds, resulting in improvement of fixability and image storability (image stability). Further, it is considered that owing to a structure with a specific substituent at each of two ortho positions, compatibility with a binder resin is improved to enhance the meltability of a toner when the compound is used for the toner, so that image storability can be secured.

Hereinafter, the compound represented by the general formula (1) will be further described.

($Z_1$ and $Z_2$)

In an embodiment of the present invention, $Z_1$ and $Z_2$ are N or CH, provided that $Z_1 \neq Z_2$, as described above. When $Z_1$ is CH and $Z_2$ is N, a further excellent photo-meltability tends to be obtained, which is more preferred.

($R_1$ and $R_2$)

In an embodiment of the present invention, $R_1$ is an aromatic hydrocarbon group having a substituent $R_a$ selected from the group consisting of an alkyl group, an alkoxy group and a halogen atom at each of two ortho positions with respect to $Z_1$; and $R_2$ is a substituted or unsubstituted aromatic heterocyclic group.

In an embodiment of the present invention, the aromatic hydrocarbon group is not particularly limited as long as it has a predetermined substituent $R_a$ at each of two ortho positions with respect to $Z_1$, an aromatic hydrocarbon group having 6 to 30 carbon atoms is preferred, and examples thereof include a phenyl group, a naphthyl group, an anthracenyl group, a phenanthrenyl group, a pyrenyl group or a biphenyl group, or the like. Such a compound is more effectively fluidized and non-fluidized. In particular, a phenyl group, a naphthyl group or a phenanthrenyl group is preferred from the viewpoint of easily developing packing between molecules, exhibiting high thermal mobility when trans-cis isomerization occurs, and easily inducing a fluidization phenomenon.

The number of carbons in the alkyl group as $R_a$ is not particularly limited, and the alkyl group is, for example, an alkyl group having 1 to 10 carbon atoms, preferably an alkyl group having 1 to 5 carbon atoms. The number of carbon atoms in the alkoxy group as $R_a$ is not particularly limited, and the alkoxy group is, for example, an alkoxy group having 1 to 10 carbon atoms, preferably an alkoxy group having 1 to 5 carbon atoms. When the number of carbon atoms is within the above-described ranges, the effects of the present invention are remarkably obtained. In addition, synthesis is easy, which is preferred. Therefore, in a preferred embodiment of the present invention, $R_a$ is an alkyl group having 1 to 5 carbon atoms, an alkoxy group having 1 to 5 carbon atoms, or a halogen atom. In particular, $R_a$ is preferably an alkyl group having 1 to 5 carbon atoms or an alkoxy group having 1 to 5 carbon atoms because fluidization is more likely to occur, and the compound exhibits further excellent fixability and image stability when used for a toner.

Substituents $R_a$ present at two ortho positions with respect to $Z_1$ are each independently selected from the group consisting of an alkyl group, an alkoxy group and a halogen atom. That is, the two substituents $R_a$ may be the same or different. It is preferred that the two substituents $R_a$ be each selected from the group consisting of an alkyl group having 1 to 5 carbon atoms, an alkoxy group having 1 to 5 carbon atoms, and a halogen atom.

Examples of the alkyl group having 1 to 10 carbon atoms include a methyl group, an ethyl group, a n-propyl group, a n-butyl group, an isobutyl group, a n-pentyl group, a n-hexyl group, a n-heptyl group, a n-octyl group, a n-nonyl group and a n-decyl group, isopropyl group, sec-buthyl group, t-butyl group, and the like. Examples of the alkoxy group having 1 to 10 carbon atoms include a methoxy group, an ethoxy group, a n-propoxy group, a n-butoxy group, a n-pentyloxy group, a n-hexyloxy group, a n-heptyloxy group, a n-octyloxy group, a n-nonyloxy group, a n-decyloxy group, a 1-methylpentyloxy group, a 4-methyl-2-pentyloxy group, and the like. Examples of the halogen atom include a fluorine atom, a chlorine atom, a bromine atom, an iodine atom, and the like.

In an embodiment of the present invention, the aromatic heterocyclic group is not particularly limited, and one having 2 to 30 carbon atoms is preferred. In addition, one having a high electron donating property is preferred. In a preferred embodiment of the present invention, $R_2$ is a thienyl group, a furanyl group, a pyrrolyl group, a pyrazolyl group, an imidazolyl group, a pyridyl group, a pyrimidinyl group, a pyrazinyl group, a triazinyl group, a benzothienyl group, a benzimidazolyl group, an indolyl group, an isoindolyl group, a quinolinyl group, an isoquinolinyl group, a quinazolinyl group, a quinoxalinyl group, a naphthyridinyl group, an acridinyl group, a carbazolyl group or a dibenzothienyl group, which may be substituted or unsubstituted. Such a compound is more effectively fluidized and non-fluidized.

In an embodiment of the present invention, the aromatic hydrocarbon group may have a substituent in addition to $R_a$. That is, the aromatic hydrocarbon group may have a substituent at a position other than two ortho positions with respect to $Z_1$. The aromatic heterocyclic group may be unsubstituted or may have a substituent. The substituent is not particularly limited, and examples thereof include a halogen atom, a cyano group, a nitro group, an amino group, an alkyl group having 1 to 18 carbon atoms, an alkoxy group having 1 to 18 carbon atoms, an alkylamino group having 1 to 10 carbon atoms, a dialkylamino group having 2 to 10 carbon atoms, an acyl group having 2 to 19 carbon atoms, and an alkoxycarbonyl group having 2 to 19 carbon atoms. The substituent is preferably a halogen atom, a cyano group, a nitro group, an alkyl group having 1 to 18 carbon atoms, an alkoxy group having 1 to 18 carbon atoms, a dialkylamino group having 2 to 10 carbon atoms, an acyl group having 2 to 19 carbon atoms, or an alkoxycarbonyl group having 2 to 19 carbon atoms.

As described above, the optical phase transition of the azomethine compound is considered to be caused by disorder of the crystal structure due to cis-trans isomerization as in the azobenzene compound. In general, since the azomethine compound has a strong n-n interaction between molecules, the optical phase transition occurs only at the outermost surface of the crystal structure. In this context, when the aromatic hydrocarbon group or the aromatic heterocyclic group each represented by $R_1$ or $R_2$ in the general formula (1) has a substituent, the azomethine compound of the present invention forms a specific crystal structure in which, in a periodic structure dominated by the π-π interaction, a structure isotropically disturbed by thermal motion of these substituents coexists. Therefore, when the cis-trans isomerization reaction locally proceeds and the n-n interaction of the azomethine moiety is reduced, isotropic melting occurs in a chain manner in the entire system. Therefore, it is considered that cis-trans isomerization is more likely to proceed, and fluidization is more likely to occur.

In particular, it is preferred that in the general formula (1), $R_1$ be a phenyl group further having a substituent selected from the group consisting of an alkyl group having 1 to 18 carbon atoms, an alkoxy group having 1 to 18 carbon atoms, a dialkylamino group having 2 to 10 carbon atoms, an acyl group having 2 to 19 carbon atoms, and an alkoxycarbonyl group having 2 to 19 carbon atoms at a para position with respect to $Z_1$. Such a structure induces generation of lattice defects, development of free volume, reduction of the n-n interaction, and the like, which act favorably for cis-trans isomerization. Therefore, it is considered that cis-trans isomerization is more likely to proceed, and fluidization is more likely to occur. In particular, introduction of these substituents at the para-position of the benzene ring facilitates collapse of crystals, improves the photo-meltability, and further enhances fixability and further improve image stability when the compound is used for a toner. Among the above-mentioned groups, an alkyl group having 1 to 18 carbon atoms, an alkoxy group having 1 to 18 carbon atoms, or a dialkylamino group having 2 to 10 carbon atoms is more preferred because of higher thermal mobility.

As to the number of carbon atoms in the substituent, the alkyl group is more preferably an alkyl group having 1 to 12 carbon atoms, still more preferably an alkyl group having 4 to 12 carbon atoms. The alkoxy group is more preferably an alkoxy group having 1 to 12 carbon atoms, still more preferably an alkoxy group having 4 to 12 carbon atoms. The dialkylamino group is more preferably a dialkylamino group having 2 to 8 carbon atoms, still more preferably a dialkylamino group having 4 to 6 carbon atoms. The acyl group is more preferably an acyl group having 2 to 13 carbon atoms, still more preferably an acyl group having 5 to 13 carbon atoms. In addition, the alkoxycarbonyl group is more preferably an alkoxycarbonyl group having 2 to 13 carbon atoms, still more preferably an alkoxycarbonyl group having 5 to 13 carbon atoms. Introduction of a long-chain substituent facilitates collapse of crystals, improves the photomeltability, and further improves fixability and image stability when the compound is used for a toner.

Examples of the alkyl group having 1 to 18 carbon atoms are not particularly limited, and include linear alkyl groups such as a methyl group, an ethyl group, a n-propyl group, a n-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, and a n-hexadecyl group; and branched alkyl groups such as an isopropyl group, a sec-butyl group, an isobutyl group, a t-butyl group, a 1-methylpentyl group, a 4-methyl-2-pentyl group, a 3,3-dimethylbutyl group, a 2-ethylbutyl group, a 1-methylhexyl group, a t-octyl group, a 1-methylheptyl group, a 2-ethylhexyl group, a 2-propylpentyl group, a 2,2-dimethylheptyl group, a 2,6-dimethyl-4-heptyl group, a 3,5,5-trimethylhexyl group, a 1-methyldecyl group, and a 1-hexylheptyl group.

Examples of the alkoxy group having 1 to 18 carbon atoms include linear alkoxy groups such as a methoxy group, an ethoxy group, a n-propoxy group, a n-butoxy group, a n-pentyloxy group, a n-hexyloxy group, a n-heptyloxy group, a n-octyloxy group, a n-nonyloxy group, a n-decyloxy group, a n-undecyloxy group, a n-dodecyloxy group, a n-tridecyloxy group, a n-tetradecyloxy group, a n-pentadecyloxy group, and a n-hexadecyloxy group; and branched alkoxy groups such as a 1-methylpentyloxy group, a 4-methyl-2-pentyloxy group, a 3,3-dimethylbutyloxy group, a 2-ethylbutyloxy group, a 1-methylhexyloxy group, a t-octyloxy group, a 1-methylheptyloxy group, a 2-ethylhexyloxy group, a 2-propylpentyloxy group, a 2,2-dimethylheptyloxy group, a 2,6-dimethyl-4-heptyloxy group, a 3,5,5-trimethylhexyloxy group, a 1-methyldecyloxy group, and a 1-hexylheptyloxy group.

Examples of the alkylamino group having 1 to 10 carbon atoms include a methylamino group, an ethylamino group, a n-propylamino group, a n-butylamino group, an isobutylamino group, a n-hexylamino group, a n-heptylamino group, a n-octylamino group, a n-nonylamino group, a n-decylamino group, and the like.

Examples of the dialkylamino group having 2 to 10 carbon atoms include a dimethylamino group, a diethylamino group, a di-n-propylamino group, a di-n-butylamino group, a di-isobutylamino group, a methylethylamino group, and the like.

Examples of the acyl group having 2 to 19 carbon atoms include saturated or unsaturated, linear or branched acyl groups, and examples thereof include an acetyl group, a propanoyl group (propionyl group), a butanoyl group (butyryl group), an isobutanoyl group (isobutyryl group), a pentanoyl group (valeryl group), an isopentanoyl group (isovaleryl group), a sec-pentanoyl group (2-methylbutyryl group), a t-pentanoyl group (pivaloyl group), a hexanoyl group, a heptanoyl group, an octanoyl group, a t-octanoyl group (2,2-dimethylhexanoyl group), a 2-ethylhexanoyl group, a nonanoyl group, an isononanoyl group, a decanoyl group, an isodecanoyl group, an undecanoyl group, a lauroyl group, a myristoyl group, a palmitoyl group, a stearoyl group, a behenoyl group, an undecylenoyl group, an oleoyl group, and the like.

Examples of the alkoxycarbonyl having 2 to 19 carbon atoms include those that are linear or branched, and examples thereof include linear alkoxycarbonyl groups such as a methoxycarbonyl group, an ethoxycarbonyl group, a n-butoxycarbonyl group, a n-hexyloxycarbonyl group, a n-heptyloxycarbonyl group, a n-octyloxycarbonyl group, a n-nonyloxycarbonyl group, a n-decyloxycarbonyl group, a n-undecyloxycarbonyl group, a n-dodecyloxycarbonyl group, a n-tridecyloxycarbonyl group, a n-tetradecyloxycarbonyl group, a n-pentadecyloxycarbonyl group, and a n-hexadecyloxycarbonyl group; and branched alkoxycarbonyl groups such as a 1-methylpentyloxycarbonyl group, a 4-methyl-2-pentyloxycarbonyl group, a 3,3-dimethylbutyloxycarbonyl group, a 2-ethylbutyloxycarbonyl group, a 1-methylhexyloxycarbonyl group, a t-octyloxycarbonyl group, a 1-methylheptyloxycarbonyl group, a 2-ethylhexyloxycarbonyl group, a 2-propylpentyloxycarbonyl group, a 2,2-dimethylheptyloxycarbonyl group, a 2,6-dimethyl-4-heptyloxycarbonyl group, a 3,5,5-trimethylhexyloxycarbonyl group, a 1-methyldecyloxycarbonyl group and a 1-hexylheptyloxycarbonyl group.

In an embodiment of the present invention, it is preferred that in the compound represented by the general formula (1), at least one carbon atom bonded adjacent to a carbon atom directly bonded to $Z_2$ is bonded to a hydrogen atom in the aromatic heterocyclic group of $R_2$. This further stabilizes the cis isomer, so that fluidization associated with photoisomerization is more effectively induced to obtain the effects of the present invention more remarkably. More preferably, both two carbon atoms bonded adjacent to a carbon atom directly bonded to $Z_2$ are bonded to hydrogen atoms in the aromatic heterocyclic group of $R_2$. This increases the probability of occurrence of an intramolecular CH-π interaction with the aromatic hydrocarbon ring in the cis isomer. Thus, the cis isomer is further stabilized to more effectively develop fluidization associated with photoisomerization, so that the effects of the present invention can be obtained more remarkably.

According to an embodiment of the present invention, a compound in which $R_2$ in the general formula (1) is represented by the following formula is provided:

[Chemical Formula 4]

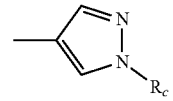

wherein $R_c$ is a hydrogen atom, an alkyl group having 1 to 18 carbon atoms, or an alkoxy group having 1 to 18 carbon atoms. This ensures efficient exhibition of desired effects of the present invention (particularly, a fixability improving effect and an image stability improving effect when the compound is used for a toner). Preferably, $R_c$ is a hydrogen atom or an alkyl group having 1 to 12 carbon atoms.

<Method for Producing Photoresponsive Compound>

A method for synthesizing the azomethine compound of the present invention is not particularly limited. For example, when an azomethine derivative is prepared in which $R_1$ contains a benzene ring having a predetermined substituent $R_a$, $Z_1$ is N, $Z_2$ is CH and $R_2$ contains a pyrazole ring, the azomethine derivative can be synthesized by reacting an aniline derivative having a predetermined substituent $R_a$ with a pyrazole carbaldehyde derivative.

In addition, for example, when an azomethine derivative is prepared in which $R_1$ contains a benzene ring having a predetermined substituent $R_a$, $Z_1$ is CH, $Z_2$ is N and $R_2$ contains a pyrazole ring, the azomethine derivative can be synthesized by reacting a benzaldehyde derivative having a predetermined substituent $R_a$ with an aminopyrazole derivative.

Specifically, for example, a compound in which $Z_1$ is CH, $Z_2$ is N, $R_1$ is a 2,6-dimethyl-4-hexyloxyphenyl group and $R_2$ is a 1-methyl-4 pyrazolyl group in the general formula (1) can be synthesized by the following scheme.

4-Hexyloxy-2,6-dimethylbenzaldehyde and 1-methyl-1H-pyrazole-4 amine are reacted by heating and stirring in ethanol (EtOH), the reaction liquid is filtered, and the resulting powder is washed with cooled ethanol, and recrystallized with methanol/ethanol, whereby an azomethine compound as a target substance can be obtained. The temperature during heating and stirring is preferably in the range of 0° C. or more and 100° C. or less, more preferably in the range of 30° C. or more and 70° C. or less, still more preferably in the range of 40° C. or more and 60° C. or less.

[Chemical Formula 5]

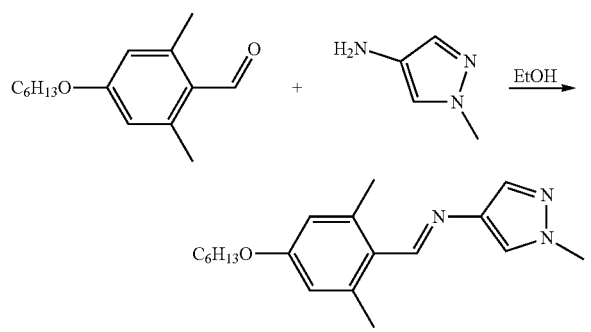

Azomethine compounds other than those described above can also be synthesized by the same method by referring to the above-described scheme and appropriately changing the raw materials.

The azomethine compound of the present invention may be used singly or in combination of two or more kinds thereof.

The molecular weight of the compound represented by the above general formula (1) in the present invention is not particularly limited, and is preferably 100 or more and less than 1000, more preferably 100 or more and 800 or less. The compound represented by the above general formula (1) in the present invention does not include a polymer. In a preferred embodiment, the compound represented by the above general formula (1) is configured not to include a repeating unit. In a preferred embodiment, the compound represented by the general formula (1) is not a compound obtained by polymerizing a monomer containing a polymerizable group.

An embodiment of the present invention is a compound represented by the following general formula (1), which is fluidized by light irradiation and reversibly non-fluidized:

[Chemical Formula 6]

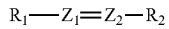

General Formula (1)

(wherein $Z_1$ and $Z_2$ are CH or N, and $Z_1 \neq Z_2$; $R_1$ is an aromatic hydrocarbon group having a substituent $R_a$ selected from the group consisting of an alkyl group, an alkoxy group and a halogen atom at each of two ortho positions with respect to $Z_1$; and $R_2$ is a substituted or unsubstituted aromatic heterocyclic group);

provided that the following compounds (1) and (2) are excluded;

(1) Compounds represented by the following Chemical Formula 1 that are reversibly fluidized and non-fluidized by being irradiated with light:

[Chemical Formula 7]

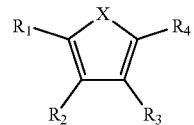

<Chemical Formula 1>

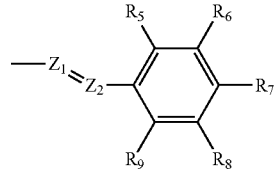

<Chemical Formula 2>

(wherein in the Chemical Formula 1,

X is $NR_{10}$, O or S;

$Z_1$ and $Z_2$ each independently represent N or CH, while $Z_1 \neq Z_2$;

$R_1$ and $R_2$ each independently represent a hydrogen atom, a halogen atom, an alkyl group, an alkoxy group, an acyl group, an alkoxycarbonyl group, a cyano group, a nitro group or a hydroxy group;

$R_3$ and $R_4$ each independently represent a group represented by the Chemical Formula 2, a hydrogen atom, a halogen atom, an alkyl group, an alkoxy group, an acyl group, an alkoxycarbonyl group, a cyano group, a nitro group or a hydroxy group, wherein either of $R_3$ and $R_4$ is a group represented by the Chemical Formula 2; and $R_{10}$ represents a hydrogen atom, a halogen atom, an alkyl group, an alkoxycarbonyl group or a hydroxy group;

in the Chemical Formula 2, $R_5$ to $R_9$ each independently represent a hydrogen atom, a halogen atom, an alkyl group, an alkoxy group, an acyl group, an alkoxycarbonyl group, a cyano group, a nitro group or a hydroxy group, wherein at least one of $R_5$ to $R_9$ represents an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms; and $R_5$ and $R_9$ are each independently selected from the group consisting of an alkyl group, an alkoxy group and a halogen atom; and (2) Compound represented by the following formula.

[Chemical Formula 8]

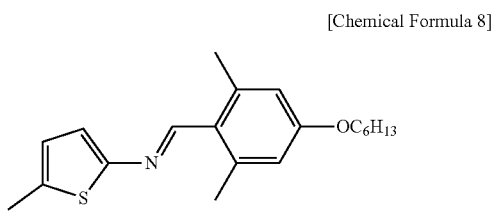

<Fluidization by Light Irradiation and Reversible Non-Fluidization>

The wavelength of irradiation light in fluidization of the compound of the present invention by light irradiation is preferably in the range of 280 nm or more and 480 nm or less, more preferably in the range of 300 nm or more and 420 nm or less, still more preferably in the range of 330 nm or more and 420 nm or less. When the wavelength is within the above-described range, crystals easily collapse (the photo-meltability is improved), and fixability is improved. At the time of fluidizing the compound, heat or pressure may be applied to the compound in addition to light irradiation to promote fluidization. When the compound is irradiated with the irradiation light having the above-mentioned wavelength, it is possible to fluidize the compound with less heat or pressure even when heat or pressure is applied. Therefore, introduction of the compound of the present invention into a toner provides a toner that can be fixed at the above-mentioned wavelength, has excellent fixability, and has high color reproducibility.

The above-mentioned wavelength range includes a part of visible light. Therefore, it is desirable that the compound of the present invention be not fluidized only by receiving sunlight (natural light) or light from illumination such as a fluorescent lamp, and further fluidized under low cost conditions in which the irradiation amount and the irradiation time are reduced as much as possible. From the above-described viewpoint, for irradiation conditions of irradiation light at the time of fluidizing the compound, the irradiation amount is preferably in the range of 0.1 J/cm$^2$ or more and 200 J/cm$^2$ or less, more preferably in the range of 0.1 J/cm$^2$ or more and 100 J/cm$^2$ or less, still more preferably in the range of 0.1 J/cm$^2$ or more and 50 J/cm$^2$ or less.

In fluidization of the compound, the compound may be heated while being irradiated with light. This enables the compound to be fluidized with a smaller irradiation amount. The heating temperature here is, for example, in the range of 20° C. or more and 200° C. or less, preferably in the range of 20° C. or more and 150° C. or less.

Meanwhile, for the conditions for non-fluidizing (resolidifying) the compound of the present invention, it is preferred to leave (in a natural environment) the compound at room temperature (in the range of 25±15° C.). In this case, it is preferred to place the compound in a dark place, but the compound may receive natural light or visible light from a fluorescent lamp or the like. It is more preferred to apply heat in the process of non-fluidizing the compound. In addition, light may be applied.

When the compound is non-fluidized by heating, the heating temperature is preferably in the range of 0° C. or more and 200° C. or less, more preferably in the range of 20° C. or more and 1.50° C. or less.

[Configuration of Toner]

An embodiment of the present invention is a toner containing the compound of the present invention. Introduction of the compound of the present invention into a toner provides a toner that can be fixed by light irradiation, has excellent fixability, and has high color reproducibility. The term "toner" refers to an aggregate of toner base particles or toner particles. The toner particles are preferably obtained by adding an external additive to the toner base particles, but the toner base particles can be used as toner particles as they are. In the present invention, when it is not necessary to particularly distinguish among the toner base particles, the toner particles, and the toner, they are also simply referred to as "toner(s)".

(Binder Resin)

The toner of the present invention preferably further contains a binder resin in addition to the predetermined azomethine compound of the present invention. It is generally known that use of an emulsion aggregation method described later as a method for producing a toner provides toner particles having a substantially uniform particle size and a substantially uniform shape. A toner can be produced without using the binder resin by using the azomethine compound alone or adding a colorant or a release agent as another additive. Combined use of the azomethine compound and the binder resin makes it possible to produce toner particles having a substantially uniform particle size and a substantially uniform shape using salting-out in the emulsion aggregation method. Therefore, the toner containing the azomethine compound and the binder resin can be applied to an electrophotographic toner more easily.

As the binder resin, a resin generally used as a binder resin that constitutes a toner can be used without limitation. As the binder resin, for example, a styrene resin, an acrylic resin, a styrene acrylic resin, a polyester resin, a silicone resin, an olefin resin, an amide resin, an epoxy resin, and the like can be used. These binder resins may be used singly or in combination of two or more kinds thereof.

Among them, it is preferred that the binder resin include at least one selected from the group consisting of a styrene resin, an acrylic resin, a styrene acrylic resin, and a polyester resin, and it is more preferred that the binder resin include at least one selected from the group consisting of a styrene acrylic resin and a polyester resin, from the viewpoint that the resin has a low viscosity when melted and has a high sharp meltability. With such an embodiment, the image intensity can be increased.

(Styrene Acrylic Resin)

The styrene acrylic resin referred to herein is a polymer containing at least a structural unit derived from a styrene monomer and a structural unit derived from a (meth)acrylic acid ester monomer. Here, the styrene monomer includes, in addition to styrene represented by the structural formula of $CH_2=CH-C_6H_5$, a monomer having a structure having a known side chain or functional group in the styrene structure.

Examples of the styrene monomer include styrene, o-methylstyrene, m-methylstyrene, p-methylstyrene, α-methylstyrene, p-phenylstyrene, p-ethylstyrene, 2,4-dimethylstyrene, p-t-butylstyrene, p-n-hexylstyrene, p-n-octylstyrene, p-n-nonylstyrene, p-n-decylstyrene, p-n-dodecylstyrene, and the like.

The (meth)acrylic acid ester monomer has, in a side chain, a functional group having an ester bond. Specifically, the (meth)acrylic acid ester monomer includes vinyl based ester compounds such as, in addition to an acrylic acid ester monomer represented by $CH_2=CHCOOR$ (wherein R is an alkyl group), a methacrylic acid ester monomer represented by $CH_2=C(CH_3)COOR$ (wherein R is an alkyl group). The (meth)acrylic acid in the (meth)acrylic acid ester monomer means acrylic acid and methacrylic acid.

Examples of the (meth)acrylic acid ester monomer include methyl (meth)acrylate, ethyl (meth)acrylate, n-propyl (meth)acrylate, isopropyl (meth)acrylate, n-butyl (meth) acrylate, isobutyl (meth)acrylate, t-butyl (meth)acrylate, n-octyl (meth)acrylate, 2-ethylhexyl (meth)acrylate, stearyl (meth)acrylate, dodecyl (meth)acrylate, phenyl (meth)acrylate, diethylaminoethyl (meth)acrylate, dimethylaminoethyl (meth)acrylate, and the like.

Both the styrene monomer and the (meth)acrylic acid ester monomer may be used singly or in combination of two or more kinds thereof.

The contents of the structural unit derived from a styrene monomer and the structural unit derived from a (meth) acrylic acid ester monomer in the styrene acrylic resin are not particularly limited, and may be appropriately adjusted from the viewpoint of controlling the softening point and the glass transition temperature of the binder resin. Specifically, the content of the structural unit derived from a styrene monomer is preferably 40 to 95 mass %, more preferably 50 to 90 mass % with respect to all the structural units forming the styrene acrylic resin. In addition, the content of the structural unit derived from a (meth)acrylic acid ester monomer is preferably 5 to 60 mass %, more preferably 10 to 50 mass % with respect to all the structural units.

The styrene acrylic resin may further contain a structural unit derived from other monomer other than the styrene monomer and the (meth)acrylic acid ester monomer as necessary. Examples of the other monomer include a vinyl monomer. Hereinafter, examples of the vinyl monomer that can be used in combination in forming the styrene acrylic copolymer referred to herein will be given, but the vinyl monomer that can be used in combination is not limited to those given below.

(1) Olefins
Ethylene, propylene, isobutylene, and the like
(2) Vinyl esters
Vinyl propionate, vinyl acetate, vinyl benzoate, and the like
(3) Vinyl ethers
Vinyl methyl ether, vinyl ethyl ether, and the like
(4) Vinyl ketones
Vinyl methyl ketone, vinyl ethyl ketone, vinyl hexyl ketone, and the like
(5) N-vinyl compounds
N-vinylcarbazole, N-vinylindole, N-vinylpyrrolidone, and the like
(6) Others
Vinyl compounds such as vinylnaphthalene and vinylpyridine, acrylic acid or methacrylic acid derivatives such as acrylonitrile, methacrylonitrile, and acrylamide, and the like.

In addition, it is also possible to produce a resin having a crosslinked structure using a polyfunctional vinyl monomer. Further, it is also possible to use a vinyl monomer having an ionic dissociation group in a side chain.

Specific examples of the ionic dissociation group include a carboxyl group, a sulfonic acid group, a phosphoric acid group, and the like. Specific examples of the vinyl monomer having the ionic dissociation group will be given below.

Specific examples of the vinyl monomer having a carboxyl group include acrylic acid, methacrylic acid, maleic acid, itaconic acid, cinnamic acid, fumaric acid, maleic acid monoalkyl ester, itaconic acid monoalkyl ester, and the like.

In the formation of the styrene acrylic resin used in the present invention, the contents of the styrene monomer and the (meth)acrylic acid ester monomer are not particularly limited, and can be appropriately adjusted from the viewpoint of controlling the softening point temperature and the glass transition temperature of the binder resin. Specifically, the content of the styrene monomer is preferably 40 to 95 mass %, more preferably 50 to 90 mass % with respect to the entire monomers that form the styrene acrylic resin. In addition, the content of the (meth)acrylic acid ester monomer is preferably 5 to 60 mass %, more preferably 10 to 50 mass % with respect to the entire monomers that form the styrene acrylic resin.

A method for forming the styrene acrylic resin is not particularly limited, and examples thereof include a method of polymerizing the monomers using a known oil-soluble or water-soluble polymerization initiator. If necessary, for example, a known chain transfer agent such as n-octyl mercaptan may be used. Examples of the oil-soluble polymerization initiator include azo or diazo polymerization initiators and peroxide polymerization initiators described below.

Examples of the azo or diazo polymerization initiator include 2,2'-azobis-(2,4-dimethylvaleronitrile), 2,2'-azobisisobutyronitrile, 1,1'-azobis(cyclohexane-1-carbonitrile), 2,2'-azobis-4-methoxy-2,4-dimethylvaleronitrile, and the like.

Examples of the peroxide polymerization initiator include benzoyl peroxide, methyl ethyl ketone peroxide, diisopropyl peroxycarbonate, cumene hydroperoxide, t-butyl hydroperoxide, di-t-butyl peroxide, dicumyl peroxide, 2,4-dichlorobenzoyl peroxide, lauroyl peroxide, 2,2-bis-(4,4-t-butylperoxycyclohexyl)propane, tris-(t-butylperoxy)triazine, and the like.

When forming styrene acrylic resin particles by an emulsion polymerization method, a water-soluble radical polymerization initiator can be used. Examples of the water-soluble radical polymerization initiator include persulfates such as potassium persulfate and ammonium persulfate, azobisaminodipropane acetate, azobiscyanovaleric acid and salts thereof, hydrogen peroxide, and the like.

The polymerization temperature varies depending on the type of monomer or polymerization initiator used, and is preferably 50° C. to 100° C., more preferably 55° C. to 90° C. The polymerization time varies depending on the type of monomer or polymerization initiator used, and is preferably 2 to 12 hours, for example.

The styrene acrylic resin particles formed by the emulsion polymerization method may have a structure including two or more layers containing resins having different compositions. As for a production method in this case, it is possible to adopt a multi-stage polymerization method in which a polymerization initiator and a polymerizable monomer are added to a dispersion liquid of resin particles prepared by an emulsion polymerization treatment (first stage polymerization) according to a routine method, and the resulting system is subjected to polymerization treatments (second and third stage polymerization).

(Polyester Resin)

The polyester resin is a polyester resin obtainable by a polycondensation reaction of a divalent or higher carboxylic acid (polyvalent carboxylic acid component) and a dihydric or higher-hydric alcohol (polyhydric alcohol component). The polyester resin may be amorphous or crystalline.

The valences of the polyvalent carboxylic acid component and the polyhydric alcohol component are preferably respectively 2 to 3, more preferably respectively 2. That is, it is preferred that the polyvalent carboxylic acid component contains a dicarboxylic acid component, and it is preferred that the polyhydric alcohol component contains a diol component.

Examples of the dicarboxylic acid component include saturated aliphatic dicarboxylic acids such as oxalic acid, malonic acid, succinic acid, glutaric acid, adipic acid, pimelic acid, suberic acid, azelaic acid, sebacic acid, 1,9-nonanedicarboxylic acid, 1,10-decanedicarboxylic acid (dodecanedioic acid), 1,11-undecanedicarboxylic acid, 1,12-dodecanedicarboxylic acid, 1,13-tridecanedicarboxylic acid, 1,14-tetradecanedicarboxylic acid, 1,16-hexadecanedicarboxylic acid, and 1,18-octadecanedicarboxylic acid; unsaturated aliphatic dicarboxylic acids such as methylene succinic acid, fumaric acid, maleic acid, 3-hexenedioic acid, 3-octenedioic acid, and dodecenylsuccinic acid; and unsaturated aromatic dicarboxylic acids such as phthalic acid, terephthalic acid, isophthalic acid, t-butylisophthalic acid, tetrachlorophthalic acid, chlorophthalic acid, nitrophthalic acid, p-phenylenediacetic acid, 2,6-naphthalenedicarboxylic acid, 4,4'-biphenyldicarboxylic acid and anthracenedicarboxylic acid; and the like, and lower alkyl esters or acid anhydrides of these can also be used. The dicarboxylic acid component may be used singly or as mixtures of two or more kinds thereof.

In addition, trivalent or higher-valent polyvalent carboxylic acids such as trimellitic acid and pyromellitic acid, anhydrides or alkyl esters having 1 to 3 carbon atoms of these, and the like can also be used.

Examples of the diol component include saturated aliphatic diols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol, 1,14-tetradecanediol, 1,18-octadecanediol, 1,20-eicosanediol, and neopentyl glycol; unsaturated aliphatic diols such as 2-butene-1,4-diol, 3-butene-1,4-diol, 2-butyne-1,4-diol, 3-butyne-1,4-diol, and 9-octadecene-7,12-diol; and aromatic diols including bisphenols such as bisphenol A and bisphenol F, and alkylene oxide adducts of bisphenols such as ethylene oxide adducts and propylene oxide adducts of these bisphenols. Derivatives thereof can also be used. The diol component may be used singly or as mixtures of two or more kinds thereof.

A method for producing the polyester resin is not particularly limited, and the polyester resin can be produced by polycondensation (esterification) of the polyvalent carboxylic acid component and the polyhydric alcohol component using a known esterification catalyst.

Examples of the catalyst that can be used in the production of the polyester resin include alkali metal compounds of sodium, lithium, and the like; compounds containing Group 2 elements such as magnesium and calcium; compounds of metals such as aluminum, zinc, manganese, antimony, titanium, tin, zirconium, and germanium; phosphorus acid compounds; phosphoric acid compounds; amine compounds; and the like. Specifically, examples of the tin compound include dibutyltin oxide, tin octylate, tin dioctylate, salts thereof, and the like. Examples of the titanium compound include titanium alkoxides such as tetra-normal-butyl titanate ($Ti(O-n-Bu)_4$), tetraisopropyl titanate, tetramethyl titanate, and tetrastearyl titanate; titanium acylates such as polyhydroxytitanium stearate; and titanium chelates such as titanium tetraacetylacetonate, titanium lactate, and titanium triethanolaminate; and the like. Examples of the germanium compound include germanium dioxide and the like. Further, examples of the aluminum compound include polyaluminum hydroxide, aluminum alkoxide, tributyl aluminate, and the like. These may be used singly or in combination of two or more kinds thereof.

The polymerization temperature is not particularly limited, and is preferably 70 to 250° C. The polymerization time is also not particularly limited, and is preferably 0.5 to 10 hours. During the polymerization, the pressure in the reaction system may be reduced as necessary.

When the toner according to the present invention contains a binder resin, the content of the azomethine compound depends on the compound species or the resin species, and is preferably in the range of azomethine compound:binder resin=5:95 to 95:5 (mass ratio), preferably in the range of 10:90 to 90:10 (mass ratio), more preferably in the range of 10:90 to 80:20 (mass ratio), still more preferably in the range of 10:90 to 70:30 (mass ratio), from the viewpoint of fixability and color reproducibility. When the content is within the above-mentioned range, the optical phase transition of the compound having an azomethine moiety is likely to occur, and a sufficient softening rate of the toner is achieved by light irradiation. When two or more kinds of azomethine compounds are used, it is preferred that the total amount thereof be in the above-described range. When two or more kinds of binder resins are used, it is preferred that the total amount thereof be in the above-described range.

The glass transition temperature (Tg) of the toner is preferably 25 to 100° C., more preferably 30 to 80° C. from the viewpoint of fixability, heat-resistant storage stability, and the like. When the toner contains the binder resin, the glass transition temperature (Tg) of the toner can be adjusted by the content of the binder resin, the type and the molecular weight of the binder resin, and the like.

The toner of the present invention may be particles having a single layer structure or particles having a core-shell structure. The type of the binder resin used in the core particles and the shell portion of the core-shell structure is not particularly limited.

<Colorant>

The toner of the present invention may further contain a colorant. Since the compound of the present invention is not significantly colored, a toner having high color reproducibility of the colorant can be obtained. As for the colorant, generally known dyes and pigments can be used.

Examples of the colorant for obtaining a black toner include carbon black, a magnetic material, iron-titanium composite oxide black, and the like, and examples of the carbon black include channel black, furnace black, acetylene black, thermal black, lamp black, and the like. Examples of the magnetic material include ferrite, magnetite, and the like.

Examples of the colorant for obtaining a yellow toner include dyes such as C.I. Solvent Yellow 19, 44, 77, 79, 81, 82, 93, 98, 103, 104, 112, and 162; and pigments such as C.I. Pigment Yellow 14, 17, 74, 93, 94, 138, 155, 180, and 185.

Examples of the colorant for obtaining a magenta toner include dyes such as C.I. Solvent Red 1, 49, 52, 58, 63, 111, and 122; and pigments such as C.I. Pigment Red 5, 48:1, 53:1, 57:1, 122, 139, 144, 149, 166, 177, 178, and 222.

Examples of the colorant for obtaining a cyan toner include dyes such as C.I. Solvent Blue 25, 36, 60, 70, 93, and 95; and pigments such as C.I. Pigment Blue 1, 7, 15, 15:3, 60, 62, 66, and 76.

The colorant for obtaining the toner of each color may be used singly or in combination of two or more kinds thereof for each color.

The content of the colorant is preferably 0.5 to 20 mass %, more preferably 2 to 10 mass %, in the toner particles (toner base particles) before the addition of the external additive.

<Release Agent>

The toner of the present invention may further contain a release agent. Introduction of the release agent into a toner provides a toner that exhibits more excellent fixability and high color reproducibility when being subjected to heat fixing together with light irradiation.

The release agent used is not particularly limited, and various known waxes can be used. Examples of the wax include polyolefins such as low molecular weight polypropylene and polyethylene, or oxidized type low molecular weight polypropylene and polyethylene, paraffin wax, synthetic ester wax, and the like. Among them, paraffin wax is preferably used from the viewpoint of improving the storage stability of the toner.

The content of the release agent is preferably 1 to 30 mass %, more preferably 3 to 15 mass %, in the toner base particles.

<Charge Control Agent>

The toner according to the present invention may contain a charge control agent. The charge control agent used is not particularly limited as long as it is a substance capable of imparting positive or negative charge by frictional charging and is colorless, and various known positive charge control agents and negative charge control agents can be used.

The content of the charge control agent is preferably 0.01 to 30 mass %, more preferably 0.1 to 10 mass % in the toner base particles.

The content of the compound of the present invention in the toner is not particularly limited, and is, for example, in the range of 5 to 95 mass % with respect to the total amount of the binder resin, the colorant, the release agent and the compound of the present invention that forms the toner, from the viewpoint of efficient fluidization and the image intensity.

<External Additive>

In order to improve the flowability, chargeability, cleaning property, and the like of the toner, the toner according to the present invention may be formed by adding, to the toner base particles, external additives such as a fluidizing agent and a cleaning aid that are so-called post-treatment agents.

Examples of the external additive include inorganic particles including inorganic oxide particles such as silica particles, alumina particles, and titanium oxide particles, inorganic stearic acid compound particles such as aluminum stearate particles and zinc stearate particles, and inorganic titanic acid compound particles such as strontium titanate particles and zinc titanate particles. These inorganic particles may be hydrophobized as necessary. These may be used singly or in combination of two or more kinds thereof.

Among these, as the external additives, for example, sol-gel silica particles, silica particles whose surface is hydrophobized (hydrophobic silica particles) or titanium oxide particles whose surface is hydrophobized (hydrophobic titanium oxide particles) are preferred, and it is more preferred to use at least two or more kinds of these external additives.

The number average primary particle size of the external additives is preferably in the range of 1 to 200 nm, more preferably in the range of 10 to 180 nm.

The amount of addition of these external additives is preferably 0.05 to 5 mass %, more preferably 0.1 to 3 mass % in the toner.

In an embodiment of the present invention, the amount of addition of these external additives is preferably 0.05 to 5 mass %, more preferably 0.1 to 3 mass % with respect to the toner base particles.

<Average Particle Size of Toner>

The average particle size of the toner (and the average particle size of the toner base particles) in terms of volume-based median diameter (D50) is preferably 4 to 20 μm, more preferably 5 to 15 μm. When the volume-based median diameter (D50) is within the above-mentioned range, the toner has high transfer efficiency, the halftone image quality is improved, and the image quality of thin lines, dots, and the like is improved.

The volume-based median diameter (D50) can be measured and calculated using a measuring apparatus including "Coulter Counter 3" (manufactured by Beckman Coulter, Inc.) and a computer system (manufactured by Beckman Coulter, Inc.) equipped with data processing software "Software V 3.51" connected thereto.

Specifically, 0.02 g of a measurement sample (toner or toner base particles) is added to 20 mL of a surfactant solution (for example, a surfactant solution obtained by diluting a neutral detergent containing a surfactant component 10-fold with pure water for the purpose of dispersing toner particles) to be compatible with the solution, then the resulting mixture is ultrasonically dispersed for 1 minute to prepare a dispersion liquid. This dispersion liquid is injected into a beaker containing "ISOTON II" (manufactured by Beckman Coulter, Inc.) in a sample stand with a pipette until the concentration displayed on the measuring apparatus reaches 8%.

Here, by setting the displayed concentration within the above-described range, a reproducible measurement value can be obtained. Then, in the measuring apparatus, the count number of the measured particles is set to 25000, the aperture diameter is set to 50 μm, the measurement range of 1 to 30 μm is divided into 256 sections and the frequency values are calculated, and the particle size at 50% of volume integrated fraction from the larger side is taken as the volume-based median diameter (D50).

[Method for Producing Toner]

A method for producing the toner of the present invention is not particularly limited. For example, in the case of using only the compound of the present invention as a toner, it is possible to employ a production method including pulverizing the compound using an apparatus such as a hammer mill, a feather mill, or a counter jet mill, and then classifying the resulting particles to have a desired particle size using a dry classifier such as Spin Air Sieve, Classiel, or Micron Classifier. In the case of producing a toner further containing a colorant, it is possible to dissolve the compound of the present invention and the colorant using a solvent capable of dissolving both the compound and the colorant to form a solution, then remove the solvent from the solution, and then pulverize and classify the resulting product in the same manner as in the above-mentioned method.

In particular, it is preferred that the toner containing the compound of the present invention and the binder resin and containing additives such as a colorant if necessary be produced by a production method based on an emulsion aggregation method by which the particle size and shape can be easily controlled.

Such a production method preferably includes:

(1A) a binder resin particle dispersion liquid preparation step of preparing a dispersion liquid of binder resin particles;

(1B) a compound particle dispersion liquid preparation step of preparing a dispersion liquid of particles of the compound of the present invention;

(1C) a colorant particle dispersion liquid preparation step of preparing a dispersion liquid of colorant particles as necessary;

(2) an association step of adding an aggregating agent to an aqueous medium in which the compound particles and the binder resin particles, and colorant particles if necessary are present, and causing salting-out to proceed and aggregating and fusing the particles at the same time to form associated particles;

(3) an aging step of controlling the shape of the associated particles to form toner base particles;

(4) a filtration and washing step of filtering out the toner base particles from the aqueous medium and removing a surfactant or the like from the toner base particles;

(5) a drying step of drying the washed toner base particles; and (6) an external additive adding step of adding an external additive to the dried toner base particles.

Hereinafter, steps (1A) to (1C) will be described.

(1A) Binder Resin Particle Dispersion Liquid Preparation Step

In this step, resin particles are formed by conventionally known emulsion polymerization or the like, and the resin particles are aggregated and fused to form binder resin particles. In an example, polymerizable monomers forming the binder resin are charged and dispersed in an aqueous medium, and the polymerizable monomers are polymerized by a polymerization initiator to prepare a dispersion liquid of binder resin particles.

Examples of the method for obtaining the binder resin particle dispersion liquid include, in addition to the above-mentioned method in which the polymerizable monomers are polymerized by a polymerization initiator in the aqueous medium, a method in which a dispersion treatment is performed in an aqueous medium without use of a solvent, and a method in which a crystalline resin is dissolved in a solvent such as ethyl acetate to form a solution, the solution is emulsified and dispersed in an aqueous medium using a disperser, and then the solvent is removed.

In this case, the binder resin may contain a release agent in advance as necessary. In addition, for dispersion, it is also preferable to appropriately perform polymerization in the presence of a known surfactant (for example, an anionic surfactant such as sodium polyoxyethylene (2) dodecyl ether sulfate, sodium dodecyl sulfate, or dodecylbenzenesulfonic acid).

The volume-based median diameter of the binder resin particles in the dispersion liquid is preferably 50 to 300 nm. The volume-based median diameter of the binder resin particles in the dispersion liquid can be measured by a dynamic light scattering method using "Microtrac UPA-150" (manufactured by NIKKISO CO., LTD.).

(1B) Compound Particle Dispersion Liquid Preparation Step

The compound particle dispersion liquid preparation step is a step of dispersing the compound of the present invention in a form of fine particles in an aqueous medium to prepare a dispersion liquid of the particles of the compound.

In preparing a dispersion liquid of the particles of the compound, first, an emulsion of the compound is prepared. The emulsion of the compound is obtained, for example, by a method in which the compound is dissolved in an organic solvent, and then the obtained solution is emulsified in an aqueous medium.

The method for dissolving the compound in the organic solvent is not particularly limited, and examples thereof include a method in which the compound is added to the organic solvent, and the resulting mixture is stirred and mixed so that the compound may be dissolved. The amount of addition of the compound is preferably 5 parts by mass or more and 100 parts by mass or less, more preferably 10 parts by mass or more and 50 parts by mass or less with respect to 100 parts by mass of the organic solvent.

Then, the obtained solution of the compound and an aqueous medium are mixed and stirred using a known disperser such as a homogenizer. As a result, the compound is emulsified as droplets in the aqueous medium, so that an emulsion of the compound is prepared.

The amount of addition of the solution of the compound is preferably 10 parts by mass or more and 110 parts by mass or less with respect to 100 parts by mass of the aqueous medium.

The temperature of each of the solution of the compound and the aqueous medium at the time of mixing the solution of the compound and the aqueous medium is in a temperature range below the boiling point of the organic solvent, and is preferably 20° C. or more and 80° C. or less, more preferably 30° C. or more and 75° C. or less. The temperature of the solution of the compound and the temperature of the aqueous medium at the time of mixing the solution of the compound and the aqueous medium may be the same as or different from each other, but are preferably the same as each other.

As for the stirring conditions of the disperser, when a stirring vessel of the disperser has a capacity of, for example, 1 L to 3 L, the rotation speed of the disperser is preferably 7,000 rpm or more and 20,000 rpm or less, and the stirring time is preferably 10 minutes or more and 30 minutes or less.

The dispersion liquid of the particles of the compound is prepared by removing the organic solvent from the emulsion of the compound. Examples of the method for removing the organic solvent from the emulsion of the compound include known methods such as air blowing, heating, pressure reduction, or a combination thereof.

In an example, the emulsion of the compound is heated, for example, in an atmosphere of an inert gas such as nitrogen at preferably 25° C. or more and 90° C. or less, more preferably 30° C. or more and 80° C. or less, until for example about 80 mass % or more and 95 mass % or less of the initial amount of the organic solvent is removed (e.g. for 20 to 150 minutes), whereby the organic solvent is removed. As a result, the organic solvent is removed from the aqueous medium to prepare a dispersion liquid of particles of the compound in which the particles of the compound is dispersed in the aqueous medium.

It is preferred that the mass average particle size of the particles of the compound in the dispersion liquid of the particles of the compound be 90 nm or more and 1200 nm or less. The mass average particle size can be set within the above-mentioned range by appropriately adjusting the viscosity when the compound is blended in the organic solvent, the blend ratio between the solution of the compound and the aqueous medium, the stirring speed of the disperser during the preparation of an emulsion of the compound, and the like. The mass average particle size of the particles of the compound in the dispersion liquid of the particles of the compound can be measured using Microtrac UPA-150 (manufactured by NIKKISO CO., LTD.) or an electrophoretic light scattering photometer "ELS-800" (manufactured by Otsuka Electronics Co., Ltd.).

<Organic Solvent>

The organic solvent used in this step is not particularly limited as long as the solvent can dissolve the compound. Specific examples of the organic solvent include esters such as ethyl acetate and butyl acetate, ethers such as diethyl ether, diisopropyl ether, and tetrahydrofuran, ketones such as acetone and methyl ethyl ketone, saturated hydrocarbons such as hexane and heptane, and halogenated hydrocarbons such as dichloromethane, dichloroethane, and carbon tetrachloride.

These organic solvents may be used singly or as mixtures of two or more kinds thereof. Among these organic solvents, ketones and halogenated hydrocarbons are preferred, and methyl ethyl ketone and dichloromethane are more preferred.

<Aqueous Medium>

Examples of the aqueous medium used in this step include water, an aqueous medium containing water as a main component, in which a water-soluble solvent such as an alcohol and a glycol, or optional components such as a surfactant and a dispersant are incorporated, and the like. The aqueous medium used is preferably a mixture of water and a surfactant.

Examples of the surfactant include a cationic surfactant, an anionic surfactant, a nonionic surfactant, and the like. Examples of the cationic surfactant include dodecylammonium chloride, dodecylammonium bromide, dodecyltrimethylammonium bromide, dodecylpyridinium chloride, dodecylpyridinium bromide, hexadecyltrimethylammonium bromide, and the like. Examples of the anionic surfactant include fatty acid soaps such as sodium stearate and sodium dodecanoate, sodium dodecylbenzenesulfonate, sodium dodecyl sulfate, and the like. Examples of the nonionic surfactant include polyoxyethylene dodecyl ether, polyoxyethylene hexadecyl ether, polyoxyethylene nonylphenyl ether, polyoxyethylene dodecyl ether, polyoxyethylene sorbitan monooleate ether, monodecanoyl sucrose, and the like.

These surfactants may be used singly or in combination of two or more kinds thereof. Among the surfactants, an anionic surfactant is preferably used, and sodium dodecylbenzenesulfonate is more preferably used.

The amount of addition of the surfactant is preferably 0.01 part by mass or more and 10 parts by mass or less, more preferably 0.04 part by mass or more and 1 part by mass or less, in terms of a solid content, with respect to 100 parts by mass of the aqueous medium.

(1C) Colorant Particle Dispersion Liquid Preparation Step

The colorant particle dispersion liquid preparation step is a step of dispersing a colorant in a form of fine particles in an aqueous medium to prepare a colorant particle dispersion liquid.

The colorant can be dispersed using mechanical energy. The number-based median diameter of the colorant particles in the dispersion liquid is preferably 10 to 300 nm, more preferably 50 to 200 nm. The number-based median diameter of the colorant particles can be measured using an electrophoretic light scattering photometer "ELS-800" (manufactured by Otsuka Electronics Co., Ltd.).

The steps from the association step (2) to the external additive adding step (6) can be performed according to various conventionally known methods.

Meanwhile, the aggregating agent used in the association step (2) is not particularly limited, but an aggregating agent selected from metal salts is suitably used. Examples of the metal salt include monovalent metal salts such as salts of alkali metals including sodium, potassium, and lithium; divalent metal salts such as salts of calcium, magnesium, manganese, and copper; and trivalent metal salts such as salts of iron and aluminum; and the like. Specific examples of the metal salt include sodium chloride, potassium chloride, lithium chloride, calcium chloride, magnesium chloride, zinc chloride, copper sulfate, magnesium sulfate, manganese sulfate, and the like. Among these, it is particularly preferred to use a divalent metal salt because the aggregation can proceed with a smaller amount of the salt. These aggregating agents may be used singly or in combination of two or more kinds thereof.

[Developer]

It is conceivable that the toner according to the present invention will be used, for example, as a one-component magnetic toner containing a magnetic material, a two-component developer containing a mixture of the toner and a so-called carrier, or a nonmagnetic toner by itself, and any of them can be suitably used.

As for the magnetic material, for example, magnetite, γ-hematite, various ferrites, or the like can be used.

As for the carrier contained in the two-component developer, it is possible to use magnetic particles made of a conventionally known material such as metals including iron, steel, nickel, cobalt, ferrite, and magnetite, and alloys of these metals with a metal such as aluminum or lead.

The carrier may be a coated carrier obtained by coating the surface of magnetic particles with a coating agent such as a resin, or a resin dispersion type carrier obtained by dispersing a magnetic material powder in a binder resin. The coating resin is not particularly limited, and for example, an olefin resin, an acrylic resin, a styrene resin, a styrene acrylic resin, a silicone resin, a polyester resin, a fluororesin, or the like is used. In addition, the resin for forming the resin dispersion type carrier particles is not particularly limited, and a known resin can be used. For example, an acrylic resin, a styrene acrylic resin, a polyester resin, a fluororesin, a phenol resin, and the like can be used.

The volume-based median diameter of the carrier is preferably 20 to 100 μm, more preferably 25 to 80 μm. The volume-based median diameter of the carrier can be typically measured by a laser diffraction type particle size distribution analyzer "HELOS" (manufactured by Sympatec GmbH) equipped with a wet disperser.

The mixed amount of the toner is preferably 2 to 10 mass % with respect to 100 mass % in total of the toner and the carrier.

[Image Forming Method]

The toner of the present invention can be used in various known electrophotographic image forming methods. For example, the toner can be used in a monochrome image forming method or a full-color image forming method. The full-color image forming method can be applied to any image forming method such as a four-cycle image forming method in which four kinds of color developing devices respectively for yellow, magenta, cyan, and black, and one photoreceptor are used, or a tandem image forming method in which an image forming unit is provided for each color, the image forming unit including a color developing device and a photoreceptor for each color.

That is, an image forming method according to an embodiment of the present invention includes the steps of: 1) forming a toner image containing the toner of the present invention on a recording medium; and 2) irradiating the toner image with light to soften the toner image. With such an embodiment, excellent fixability is exhibited, so that higher image quality is obtained.

Step 1)

In this step, a toner image containing the toner of the present invention is formed on a recording medium.

(Recording Medium)

The recording medium is a member for holding a toner image. Examples of the recording medium include plain paper, high quality paper, coated printing paper such as art paper and coated paper, commercially available Japanese paper and postcard paper, resin films for OHP use or for packaging materials, cloth, and the like.

The recording medium may have a sheet shape (sheet-like shape) having a predetermined size, or an elongated shape that is wound in a roll shape after the toner image is fixed to the recording medium.

As described later, the toner image can be formed, for example, by transfer of the toner image on a photoreceptor onto the recording medium.

Step 2)

In this step, the formed toner image is irradiated with light to soften the toner image. As a result, the toner image can be made to adhere onto the recording medium.

The wavelength of the light irradiated is not particularly limited as long as the light can sufficiently soften the toner image by the photothermal conversion caused by the compound in the toner, and is preferably 280 nm or more and 480 nm or less. When the wavelength is within the above-mentioned range, the toner image can be softened more efficiently. From a similar viewpoint, the light irradiation amount is preferably 0.1 to 200 $J/cm^2$, more preferably 0.1 to 100 $J/cm^2$, still more preferably 0.1 to 50 $J/cm^2$.

As described later, the light irradiation can be performed using a light source such as a light emitting diode (LED) or a laser light source. As described later, heating may be further performed together with light irradiation.

After step 2), a step of pressurizing the softened toner image (step 3)) may be further performed if necessary. With such an embodiment, fixability is improved.

Step 3)

In this step, the softened toner image is pressurized.

The pressure at the time of pressurizing the toner image on the recording medium is not particularly limited, but is preferably 0.01 to 5.0 MPa, more preferably 0.05 to 1.0 MPa. When the pressure is 0.01 MPa or more, the toner image can be largely deformed, so that the contact area between the toner image and the recording sheet S is increased, and the image fixability can be further improved easily. In addition, when the pressure is 5.0 MPa or less, shock noise at the time of pressurization can be reduced.

The pressurizing step may be performed before or in parallel to the step of irradiating the toner image with light to soften the toner image (the aforementioned step 2)), but it is preferred to perform the pressurizing step after light irradiation because it is possible to pressurize the toner image softened in advance, and as a result, image fixability is further improved.

In the pressurizing step, the softened toner image may be further heated. That is, the pressurizing step may be performed with heating the toner image. The temperature (e.g. temperature of the pressurizing member) at this time is preferably 15° C. or more, more preferably 20° C. or more, still more preferably more than 20° C., even more preferably 30° C. or more, even more preferably 40° C. or more. With such an embodiment, fixability is remarkably improved. The upper limit is not particularly limited, and is, for example, 200° C. or less, 150° C. or less, or 100° C. or less.

The temperature for heating the toner image (surface temperature of the toner image during heating) is preferably (Tg+20°) C. to (Tg+100°) C., more preferably (Tg+25°) C. to (Tg+80°) C., where Tg is the glass transition temperature of the toner. When the surface temperature of the toner image is (Tg+20°) C. or more, the toner image is easily deformed by pressurization, and when the surface temperature is (Tg+100°) C. or less, hot offset is easily reduced. Note that the hot offset refers to a phenomenon in which, in a fixing step, part of the toner is transferred to a pressurizing member such as a roller and the toner layer is separated.

Further, before step 2), a step of heating the toner image in advance (step 4)) may be further performed as necessary. When step 4) of heating the toner image in advance is performed before step 2) in this way, sensitivity of the compound of the present invention to light can be further enhanced. As a result, sensitivity to light is less likely to be impaired even though the compound is a high-molecular weight compound, so that melting or softening of the toner image by light irradiation is likely to be promoted.

The image forming method of the present invention can be performed by using, for example, the following image forming apparatus.

FIG. 1 is a schematic configuration diagram illustrating an image forming apparatus 100 used in an image forming method according to an embodiment of the present invention. The image forming apparatus used in the present invention is not limited to the following embodiment and the illustrated example. FIG. 1 illustrates an example of a monochrome image forming apparatus 100, but the present invention can also be applied to a color image forming apparatus.

The image forming apparatus 100 is an apparatus that forms an image on a recording sheet S as a recording medium. The image forming apparatus 100 includes an image reading device 71 and an automatic document feeder 72, and forms an image on the recording sheet S conveyed by a sheet conveying system 7 through the use of an image forming unit 10, an irradiation unit 40, and a pressure-bonding unit 9.

The recording medium used in the image forming apparatus 100 is the recording sheet S, but the medium to be subjected to image formation may be other than a paper sheet.

A document d placed on a document table of the automatic document feeder 72 is scanned and exposed by an optical system of a scanning exposure device in the image reading device 71, and read by an image sensor CCD. An analog signal obtained by photoelectric conversion at the image sensor CCD is subjected to analog processing, A/D conversion, shading correction, image compression processing, and the like in an image processing unit 20, and then input to an exposure device 3 in the image forming unit 10.

The sheet conveying system 7 includes a plurality of trays 16, a plurality of sheet feeders 11, conveying rollers 12, a conveyor belt 13, and the like. Each of the trays 16 stores recording sheets S of a predetermined size, and the sheet feeder 11 of the tray 16 determined in accordance with an instruction from a control unit 90 is operated to supply a recording sheet S. The conveying rollers 12 convey the recording sheet S fed from the tray 16 by the sheet feeder 11 or the recording sheet S fed from a manual sheet feeder 15 to the image forming unit 10.

The image forming unit 10 has a configuration in which around a photoreceptor 1 and in a rotation direction of the photoreceptor 1, a charger 2, an exposure device 3, a developing unit 4, a transfer unit 5, and a cleaning unit 8 are arranged in this order.

The photoreceptor 1 as an image carrier is an image carrier having a photoconductive layer formed on a surface thereof, and is configured to be rotatable in a direction of an arrow in FIG. 1 by a driving device (not illustrated). A thermo-hygrometer 17 that detects the temperature and humidity in the image forming apparatus 100 is provided in the vicinity of the photoreceptor 1.

The charger 2 uniformly impart charges to the surface of the photoreceptor 1 to uniformly charge the surface of the photoreceptor 1. The exposure device 3 includes a beam emission source such as a laser diode, and irradiates the charged surface of the photoreceptor 1 with beam light to dissipate the charges of the irradiated portion, and forms an electrostatic latent image corresponding to image data on the photoreceptor 1. The developing unit 4 supplies a toner contained therein to the photoreceptor 1 to form a toner image based on the electrostatic latent image on the surface of the photoreceptor 1.

The transfer unit 5 faces the photoreceptor 1 with the recording sheet S interposed therebetween, and transfers the toner image to the recording sheet S. The cleaning unit 8 includes a blade 85. The blade 85 cleans the surface of the photoreceptor 1 to remove the developer remaining on the surface of the photoreceptor 1.

The recording sheet S to which the toner image has been transferred is conveyed to the pressure-bonding unit 9 by the conveyor belt 13. The pressure-bonding unit 9 is optionally installed, and applies only pressure or heat and pressure to the recording sheet S to which the toner image has been transferred by pressurizing members 91 and 92 to perform fixing processing, thereby fixing the image on the recording sheet S. The recording sheet S on which the image is fixed is conveyed to a sheet ejector 14 by the conveying rollers, and is ejected from the sheet ejector 14 to the outside of the apparatus.

In addition, the image forming apparatus 100 includes a sheet reversing unit 24, and it is possible to convey the recording sheet S having been subjected to the heat fixing processing to the sheet reversing unit 24 before the sheet ejector 14 and eject the recording sheet S with the front and back reversed, or to convey the recording sheet S with the front and back reversed to the image forming unit 10 again and form an image on both sides of the recording sheet S.

<Irradiation Unit>

Figure 2:
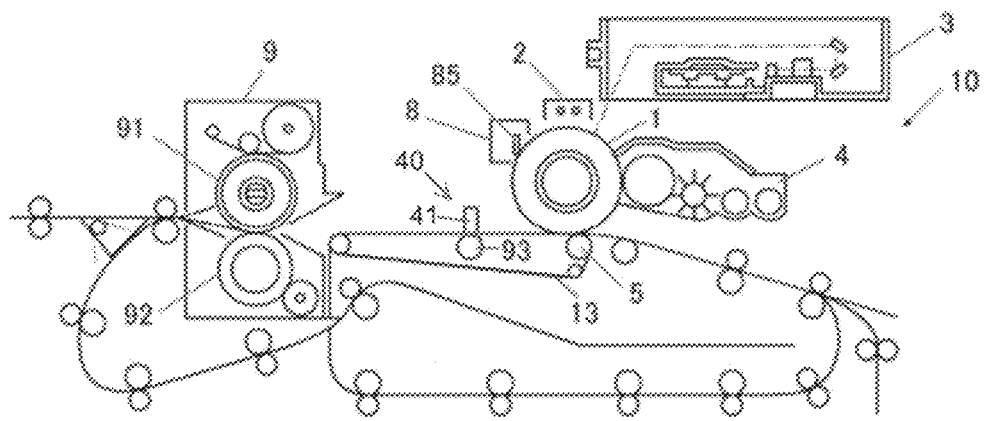
FIG. 2 is a schematic configuration diagram of an irradiation unit 40 in the image forming apparatus 100.

FIG. 2 is a schematic configuration diagram of the irradiation unit 40 in the image forming apparatus 100.

The image forming apparatus 100 according to an embodiment of the present invention includes the irradiation unit 40. The irradiation unit 40 includes a light source 41 and a heating member 93. Examples of a device that constitutes the light source 41 include a light emitting diode (LED), a laser light source, and the like.

The light source 41 irradiates the toner image formed on the recording medium with light to soften the toner image. The conditions for light irradiation are not particularly limited as long as the compound of the present invention contained in the toner of the developer is melted and fluidized. The wavelength of the light applied to the toner image may be one allowing the compound to be sufficiently fluidized, and is preferably in the range of 280 nm or more and 480 nm or less, more preferably in the range of 300 nm or more and 420 nm or less, still more preferably in the range of 330 nm or more and 420 nm or less. The light irradiation amount in the light source 41 may be one allowing the compound to be sufficiently fluidized, and is preferably in the range of 0.1 J/cm$^2$ or more and 200 J/cm$^2$ or less, more preferably in the range of 0.1 J/cm$^2$ or more and 100 J/cm$^2$ or less, still more preferably in the range of 0.1 J/cm$^2$ or more and 50 J/cm$^2$ or less.

When the toner image is irradiated with light by the light source 41 to soften the toner image, the toner image may be heated by the heating member 93 while being irradiated with light. This enables softening and melting of the toner image to more efficiently proceed. The heating temperature here is, for example, in the range of 20° C. or more and 200° C. or less, preferably in the range of 20° C. or more and 150° C. or less.

When the softened toner image is left standing at room temperature (range of 25±15° C.), heated, or irradiated with visible light, the toner image can be solidified and fixed on the recording medium. It is preferred that the step of fixing the image further include a step of pressurizing the softened toner image. In the pressurizing step, it is preferred to further heat the softened toner image.

The light source 41 applies light to a first surface of the recording sheet S, which is on the photoreceptor side and holds the toner image, and is disposed on the photoreceptor side with respect to the surface of the recording sheet S nipped between the photoreceptor 1 and the transfer roller 5 which is a transfer unit. The heating member 93 is disposed on a side opposite to the light source 41 with respect to a surface of the recording sheet S. The light source 41 and the heating member 93 are disposed along a conveyance direction of the recording sheet S (sheet conveyance direction).

The light source 41 and the heating member 93 are disposed on the downstream side in the sheet conveyance direction with respect to the nip position between the photoreceptor 1 and the transfer roller 5 and on the upstream side in the sheet conveyance direction with respect to the pressure-bonding unit 9.

According to the image forming method of an embodiment of the present invention, after the photoreceptor 1 is charged by application of a uniform potential from the charger 2, the photoreceptor 1 is scanned with a light flux emitted by the exposure device 3 based on original image data, whereby an electrostatic latent image is formed. Then, a developer that contains the toner of the present invention is supplied by the developing unit 4 onto the photoreceptor 1.

When a recording sheet S is conveyed from any of the trays 16 to the image forming unit 10 in accordance with the timing at which the toner image carried on the surface of the photoreceptor 1 reaches the position of the transfer unit 5 by the rotation of the photoreceptor 1, the toner image on the photoreceptor 1 is transferred to the recording sheet S nipped between the transfer unit 5 and the photoreceptor 1 by the transfer bias applied to the transfer unit 5.

The transfer unit 5 also serves as a pressurizing member, and can reliably bring the compound contained in the toner image into close contact with the recording sheet S while the toner image can be transferred from the photoreceptor 1 to the recording sheet S.

After the toner image is transferred to the recording sheet S, the blade 85 of the cleaning unit 8 removes the developer remaining on the surface of the photoreceptor 1.

In a process in which the recording sheet S to which the toner image has been transferred is conveyed to the pressure-bonding unit 9 by the conveyor belt 13, the light source 41 irradiates the toner image transferred to the recording sheet S with light. Since the toner image on the first surface of the recording sheet S is irradiated with the light by the light source 41, the toner image can be more reliably melted, and the fixability of the toner image to the recording sheet S can be improved.

When the recording sheet S holding the toner image is conveyed by the conveyor belt 13 and reaches the pressure-bonding unit 9, the pressurizing members 91 and 92 pressure-bond the toner image to the first surface of the recording sheet S. Since the toner image has been softened by the light applied from the light source 41 before being fixed by the pressure-bonding unit 9, energy for pressure-bonding the image to the recording sheet S can be saved. Further, in the step of solidifying the toner image and fixing the toner image on the recording medium, the toner image is pressurized by the pressurizing members 91 and 92 to further improve the fixability of the toner image on the recording sheet S.

The pressure for pressurizing the toner image is as described above. The pressurizing step may be performed before, in parallel to, or after the step of softening the toner image by light irradiation. It is preferred to perform the pressurizing step after light irradiation because it is possible to pressurize the toner image softened in advance, and image intensity is easily improved.

Further, the pressurizing member 91 can heat the toner image on the recording sheet S when the recording sheet S passes between the pressurizing members 91 and 92. The toner image softened by the light irradiation is further softened by the heating, and as a result, the fixability of the toner image to the recording sheet S is further improved.

The temperature for heating the toner image is as described above. The temperature for heating the toner image (surface temperature of the toner image) can be measured by a non-contact temperature sensor. Specifically, for example, the surface temperature of the toner image on the recording medium may be measured by installing a non-contact temperature sensor at a position where the recording medium is released from the pressurizing members.

The toner image pressure-bonded by the pressurizing members 91 and 92 is solidified and fixed on the recording sheet S.

In an embodiment of the present invention, a fixing device includes a pressure-bonding unit including a pressurizing member.

In an embodiment of the present invention, the pressurizing member includes a heating means.

In an embodiment of the present invention, the temperature of the pressurizing member is preferably 15° C. or more, more preferably 20° C. or more, still more preferably more than 20° C., even more preferably 30° C. or more, even more preferably 40° C. or more. The upper limit is not particularly limited, and is, for example, 200° C. or less, 150° C. or less, or 100° C. or less.

<Photoresponsive Adhesive>

Since the compound of the present invention is fluidized by light irradiation and reversibly non-fluidized, a photoresponsive adhesive (photosensitive adhesive) that can be repeatedly used can be produced using the compound of the present invention. For example, the compound can be applied to various adhesion techniques as a photoresponsive adhesive that is capable of repeated desorption and adhesion by light in response to a change in viscosity (friction coefficient). That is, an embodiment of the present invention is a photoresponsive adhesive containing the compound of the present invention.

The photoresponsive adhesive of the present invention can be used in temporary fixing for which the adhesive can be repeatedly used, and is also suitable for recycling utilization, but the use is not limited thereto.

<Optical Switching Material>

Since the compound of the present invention is fluidized by light irradiation and reversibly non-fluidized, an optical switching material can be produced using the compound of the present invention. The optical switching material can be produced, for example, by utilizing a change in color or polarity, mass transfer, a change in orientation, a change in viscosity, a change in surface tension, or the like due to photoisomerization. For example, in a liquid crystal material or the like, the compound can be applied to pattern drawing in which patterns can be repeatedly redrawn in response to a change in molecular orientation due to photoisomerization. In addition, for example, the surface of a polymer film can be finely processed by using a change in surface tension due to light irradiation or mass transfer caused by such change. That is, an embodiment of the present invention is an optical switching material containing the compound of the present invention.

The optical switching material of the present invention can be used in a liquid crystal display material or surface processing of a polymer film, but the use is not limited thereto.

EXAMPLES

Hereinafter, the present invention will be specifically described with reference to examples, but the present invention is not limited thereto.

Example 1: Synthesis of Compound 1

To a 100-ml four-necked flask equipped with a condenser, a nitrogen introducing tube and a thermometer, 4-hexyloxy-2,6-dimethylbenzaldehyde (5 mmol), 1-methyl-1H-pyrazole-4-amine (5 mmol) and 20 ml of ethanol were charged, and heated and stirred. The reaction liquid was filtered by suction, and the obtained powder was washed with cooled ethanol. Further, the resulting product was recrystallized with heptane to obtain Compound 1 as a target substance with a yield of 61%.

[Chemical Formula 9]

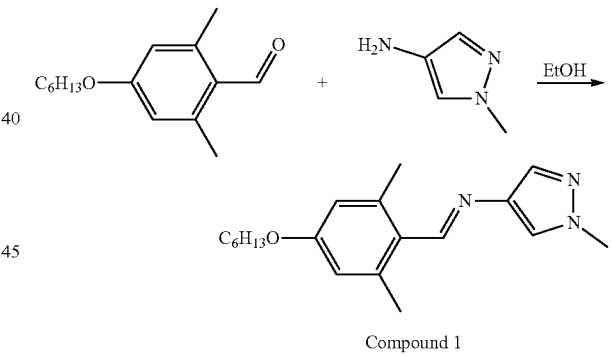

Compound 1

Production of Compound 1 was confirmed by $^1$H NMR. $^1$H NMR (400 MHz, CDCl$_3$); 8.85 ppm(s, 1H, pyrazol), 8.39 ppm(s, 1H, CH=N), 8.02 ppm(s, 1H, pyrazol), 6.83 ppm (s, 1H, aryl), 4.11 ppm(t, 2H, methylene), 3.95 ppm (s, 3H, methyl), 2.31 ppm (s, 6H, methyl), 1.81 ppm (m, 2H, methylene), 1.26 ppm (m, 6H, methylene), 0.89 ppm (t, 3H, methyl).

Examples 2 to 14 and Comparative Examples 1 to 7: Synthesis of Compounds 2 to 14 and Comparative Compounds 1 to 7

For the synthesis of Compounds 2 to 14 and Comparative Compounds 1 to 7, a target substance was obtained by performing synthesis in the same manner as in the synthesis of Compound 1 except that 4-hexyloxy-2,6-dimethylbenzaldehyde and 1-methyl-1H-pyrazole-4-amine were replaced by the corresponding raw materials described below. In addition, production of each compound was similarly confirmed by $^1$H NMR.

Synthesis of Compound 2: 4-hexyloxy-2,6-dimethylbenzaldehyde and 1-hexyl-1H-pyrazole-4-amine;
Synthesis of Compound 3: 4-hexyloxy-2,6-diethylbenzaldehyde and 1-methyl-1H-pyrazole-4-amine;
Synthesis of Compound 4: 4-hexyloxy-2,6-dipropylbenzaldehyde and 1-methyl-1H-pyrazole-4-amine;
Synthesis of Compound 5: 4-hexyloxy-2,6-dimethoxybenzaldehyde and 1-methyl-1H-pyrazole-4-amine;
Synthesis of Compound 6: 4-hexyloxy-2,6-difluorobenzaldehyde and 1-methyl-1H-pyrazole-4-amine;
Synthesis of Compound 7: 4-decyloxy-2,6-dimethylbenzaldehyde and 1-methyl-1H-pyrrol-3-amine;
Synthesis of Compound 8: 4-hexyloxy-2,6-dimethylaniline and 1-hexyl-1H-pyrrol-3-carboxyaldehyde;
Synthesis of Compound 9: 4-hexyloxy-2,6-dimethylbenzaldehyde and 1-methyl-1H-pyrrol-2-amine;
Synthesis of Compound 10: 4-hexyloxy-2,6-dimethylbenzaldehyde and 1H-indole-6-amine;
Synthesis of Compound 11: 4-hexyloxy-2,6-dimethylbenzaldehyde and 1-methyl-1H-pyrazole-3-amine;
Synthesis of Compound 12: 4-decyloxy-2,6-dimethylbenzaldehyde and 2-aminoimidazole;
Synthesis of Compound 13: 4-decyloxy-2,6-dimethylbenzaldehyde and 2-amino-5-hexylthiophene;
Synthesis of Compound 14: 4-hexyloxy-2,6-dimethylaniline and 5-methylthiophene-2-carboxyaldehyde;
Synthesis of Comparative Compound 1 (Comparative 1): 4-hexyloxy-2-methylbenzaldehyde and 1-hexyl-1H-pyrazole-4-amine;
Synthesis of Comparative Compound 2 (Comparative 2): 4-hexyloxy-2,5-dimethylbenzaldehyde and 1-methyl-1H-pyrazole-4-amine;
Synthesis of Comparative Compound 3 (Comparative 3): 4-hexyloxy-2-fluorobenzaldehyde and 1-ethyl-1H-pyrazole-4-amine;
Synthesis of Comparative Compound 4 (Comparative 4): 4-hexyloxy-2,5-dimethylamine and 1-methyl-1H-pyrazole-4-carboxyaldehyde;
Synthesis of Comparative Compound 5 (Comparative 5): 4-hexyloxy-2-fluoroamine and 1-methyl-1H-pyrazole-4-carboxyaldehyde;
Synthesis of Comparative Compound 6 (Comparative 6): 4-hexyloxy-2-methoxyamine and 1-methyl-1H-pyrazole-4-carboxyaldehyde; and
Synthesis of Comparative Compound 7 (Comparative 7): 4-hexyloxy-benzaldehyde and 1-methyl-1H-pyrrol-3-amine.

The structures of Compounds 1 to 14 and Comparative Compounds 1 to 7 are shown in Table 1 below.

Comparative Example 8: Synthesis of Comparative Compound 8

The following Comparative Compound 8 (Comparative 8, number average molecular weight Mn: 2870) was obtained by the method described in paragraphs 0217 to 0227 of JP 2014-191078 A.

[Chemical Formula 10]

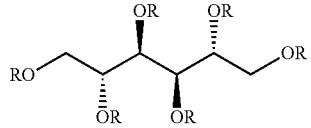

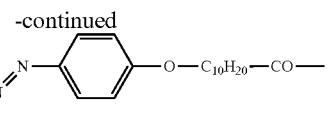

[Production of Toner]
(Production of Toner 1)
<Preparation of Styrene Acrylic Resin Particle Dispersion Liquid 1>
(First Stage Polymerization)

To a reaction vessel equipped with a stirrer, a temperature sensor, a condenser, and a nitrogen introduction device, a solution obtained by dissolving 8 parts by mass of sodium dodecyl sulfate in 3000 parts by mass of ion-exchanged water was charged, and the internal temperature was raised to 80° C. with stirring at a stirring speed of 230 rpm under a nitrogen stream. After the temperature rise, a solution obtained by dissolving 10 parts by mass of potassium persulfate in 200 parts by mass of ion-exchanged water was added, the liquid temperature was again adjusted to 80° C., a polymerizable monomer solution containing 480 parts by mass of styrene, 250 parts by mass of n-butyl acrylate, 68.0 parts by mass of methacrylic acid, and 16.0 parts by mass of n-octyl-3-mercaptopropionate was added dropwise over 1 hour, and the mixture was heated and stirred at 80° C. for 2 hours to perform polymerization, thereby preparing a styrene acrylic resin particle dispersion liquid (1A) containing styrene acrylic resin particles (1a).

(Second Stage Polymerization)

To a reaction vessel equipped with a stirrer, a temperature sensor, a condenser, and a nitrogen introduction device, a solution obtained by dissolving 7 parts by mass of sodium polyoxyethylene (2) dodecyl ether sulfate in 800 parts by mass of ion-exchanged water was charged, the solution was heated to 98° C., 260 parts by mass of the styrene acrylic resin particle dispersion liquid (1A) obtained above, and a polymerizable monomer solution obtained by dissolving, at 90° C., 245 parts by mass of styrene, 120 parts by mass of n-butyl acrylate, 1.5 parts by mass of n-octyl-3-mercaptopropionate, and 67 parts by mass of paraffin wax "HNP-11" (manufactured by NIPPON SEIRO CO., LTD.) as a release agent were then added thereto, and the mixture was mixed and dispersed for 1 hour by a mechanical disperser "CLEARMIX (registered trademark)" (manufactured by M Technique Co., Ltd.) having a circulation path to prepare a dispersion liquid containing emulsified particles (oil droplets). Then, an initiator solution obtained by dissolving 6 parts by mass of potassium persulfate in 200 parts by mass of ion-exchanged water was added to the dispersion liquid, and the resulting system was heated and stirred at 82° C. for 1 hour to perform polymerization, thereby preparing a styrene acrylic resin particle dispersion liquid (1B) containing styrene acrylic resin particles (1b).

(Third Stage Polymerization)

To the obtained styrene acrylic resin particle dispersion liquid (1B), a solution obtained by dissolving 11 parts by mass of potassium persulfate in 400 parts by mass of ion-exchanged water was added, and a polymerizable monomer solution containing 435 parts by mass of styrene, 130 parts by mass of n-butyl acrylate, 33 parts by mass of methacrylic acid and 8 parts by mass of n-octyl-3-mercaptopropionate was then added dropwise under the temperature condition of 82° C. over 1 hour. After completion of the dropwise addition, the mixture was heated and stirred over 2 hours to perform polymerization, and then cooled to 28°

C. to obtain a styrene acrylic resin particle dispersion liquid 1 containing a styrene acrylic resin 1. The glass transition temperature (Tg) of the styrene acrylic resin 1 was measured and found to be 45° C.

<Preparation of Azomethine Compound Particle Dispersion Liquid 1>

While being heated at 50° C., 80 parts by mass of dichloromethane and 20 parts by mass of Compound 1 prepared as described above were mixed and stirred to give a liquid containing Compound 1. To 100 parts by mass of the liquid, a mixed liquid of 99.5 parts by mass of distilled water warmed to 50° C. and 0.5 parts by mass of a 20 mass % aqueous sodium dodecylbenzenesulfonate solution was added. Then, the resulting mixture was stirred and emulsified at 16,000 rpm for 20 minutes using a homogenizer (manufactured by Heidolph) equipped with a shaft generator 18F to give an azomethine compound emulsion 1.

The obtained azomethine compound emulsion 1 was charged into a separable flask, and heated and stirred at 40° C. for 90 minutes with nitrogen being fed into the gas phase to remove the organic solvent, thereby obtaining an azomethine compound particle dispersion liquid 1.

<Preparation of Black Colorant Particle Dispersion Liquid (Bk-1)>

In 160 parts by mass of pure water, 11.5 parts by mass of sodium n-dodecyl sulfate was dissolved, 25 parts by mass of carbon black "MOGUL L" (manufactured by Cabot Corporation) was gradually added thereto, and the mixture was subjected to dispersion treatment using "CLEARMIX (registered trademark) W-Motion CLM-0.8 (manufactured by M Technique Co., Ltd.)" to prepare a black colorant particle dispersion liquid (Bk-1). The colorant particles in the black colorant particle dispersion liquid (Bk-1) had a volume-based median diameter of 110 nm.

(Aggregation and Fusion)

To a reactor equipped with a stirrer, a temperature sensor, and a condenser, 504 parts by mass in terms of solid content of the styrene acrylic resin particle dispersion liquid 1 prepared as described above, 216 parts by mass in terms of solid content of the azomethine compound particle dispersion liquid 1, 900 parts by mass of ion-exchanged water, and 70 parts by mass in terms of solid content of the black colorant particle dispersion liquid were charged. The temperature in the vessel was maintained at 30° C., and a 5 mol/L aqueous sodium hydroxide solution was added to adjust the pH to 10.

Then, an aqueous solution obtained by dissolving 2 parts by mass of magnesium chloride hexahydrate in 1000 parts by mass of ion-exchanged water was added dropwise under stirring over 10 minutes, and then the temperature was started to be raised. The temperature of the system was raised to 70° C. over 60 minutes, and a particle growth reaction was continued with the temperature being maintained at 70° C. In this state, the particle size of associated particles was measured with "Multisizer 3" (manufactured by Beckman Coulter, Inc.), and when the volume-based median diameter (D50) reached 6.5 μm, an aqueous solution obtained by dissolving 190 parts by mass of sodium chloride in 760 parts by mass of ion-exchanged water was added to stop the particle growth. The resulting mixture was stirred at 70° C. for 1 hour, then the temperature was further raised, and the mixture was heated and stirred at 75° C. to advance fusion of the particles. Then, the mixture was cooled to 30° C. to give a dispersion liquid of toner base particles.

The dispersion liquid of toner base particles obtained as described above was subjected to solid-liquid separation with a centrifuge to form a wet cake of the toner base particles. The wet cake was washed with ion-exchanged water at 35° C. in the centrifuge until the filtrate had an electric conductivity of 5 μS/cm, then transferred to "Flash Jet Dryer (manufactured by SEISHIN ENTERPRISE Co., Ltd.)", and dried until the water content reached 0.5 mass %, thereby producing toner base particles.

To 100 mass % of the obtained toner base particles, 1 mass % of hydrophobic silica (number average primary particle size: 12 nm) and 0.3 mass % of hydrophobic titania (number average primary particle size: 20 nm) were added and mixed using a Henschel mixer (registered trademark) to give Toner 1.

Production of Toners 2 to 18 and Toners of Comparative Examples 1 to 8

Toners 2 to 14 and toners of Comparative Examples 1 to 8 were produced in the same procedure as in the production of Toner 1 except that with respect to the production of Toner 1, Compound 1 was changed to Compounds 2 to 14 and the compounds of Comparative Examples 1 to 8, respectively. In addition, Toners 15 to 18 were produced in the same procedure except that with respect to the production of Toner 1, the mass ratio of Compound 1 to the styrene acrylic resin was changed as in Table 3 below.

(Production of Toner 19)

Toner 19 was produced in the same procedure as in the production of Toner 1 except that with respect to the production of Toner 1, the styrene acrylic resin particle dispersion liquid 1 (504 parts by mass in terms of a solid content) was changed to a polyester resin particle dispersion liquid 2 (504 parts by mass in terms of a solid content) prepared as follows, in the (Aggregation and Fusion) step.

<Production of Polyester Resin Particle Dispersion Liquid 2 containing Polyester Resin 1>

Into a 10-L four-necked flask equipped with a nitrogen introducing tube, a dehydration tube, a stirrer, and a thermocouple, 524 parts by mass of a bisphenol A propylene oxide 2 mol adduct, 105 parts by mass of terephthalic acid, 69 parts by mass of fumaric acid, and 2 parts by mass of tin octylate (an esterification catalyst) were charged, and a polycondensation reaction was performed at a temperature of 230° C. for 8 hours. Further, the polycondensation reaction was continued at 8 kPa for 1 hour, and then cooled to 160° C. to give a polyester resin 1. Using "Roundel Mill model RM" (manufactured by TOKUJU CORPORATION), 100 parts by mass of the polyester resin 1 was pulverized. The polyester resin 1 was mixed with 638 parts by mass of a 0.26 mass % aqueous sodium lauryl sulfate solution prepared in advance, and was ultrasonically dispersed at V-LEVEL, 300 μA for 30 minutes using an ultrasonic homogenizer "US-150T" (manufactured by NIHONSEIKI KAISHA LTD.) with stirring to give a polyester resin particle dispersion liquid 2. The glass transition point Tg of the polyester resin 1 was measured and found to be 42° C.

(Production of Developer)

Toners 1 to 19 and the toners of Comparative Examples 1 to 8 produced as described above were mixed with ferrite carrier particles coated with a copolymer resin of cyclohexane methacrylate and methyl methacrylate (mass ratio between monomers 1:1) and having a volume average particle size of 30 μm so as to obtain a toner particle concentration of 6 mass %, thereby obtaining Developers 1 to 19 and developers of Comparative Examples 1 to 8, respectively. Mixing was carried out for 30 minutes using a V-type mixer.

[Evaluation: Photoresponsive Adhesion Test on Compound]

Figure 3:
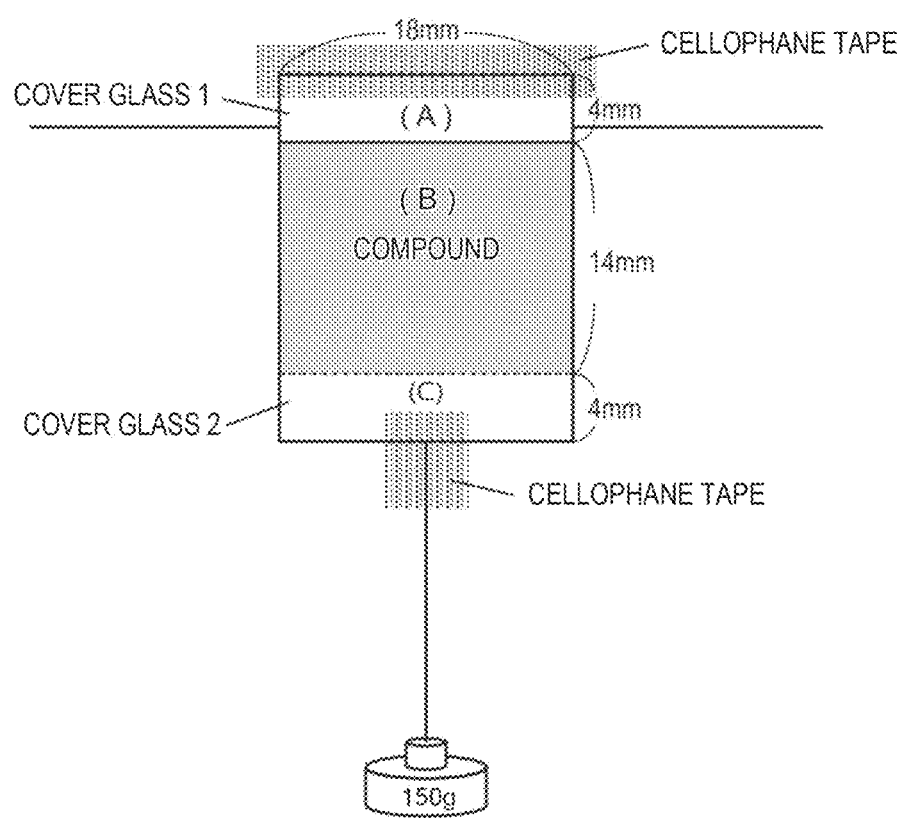
FIG. 3 is a schematic view of a device for measuring a light irradiation-associated change in adhesiveness of a compound used in a photoresponsive adhesion test in examples.

Compounds 1 to 14 prepared in examples and Comparative Compounds 1 to 8 were evaluated for changes in adhesiveness due to light irradiation by the following photoresponsive adhesion test using a device shown in FIG. 3. As shown in FIG. 3, 4 mg of a compound was placed on a 18-mm square cover glass 1 within a 6-mm radius from the center of the cover glass 1, and a cover glass 2 of the same size was placed on the cover glass 1 at a position shifted by about 4 mm in a direction parallel to the cover glass 1 so as to cover the entire compound. This was heated to melt the sample, and the cover glass 1 and the cover glass 2 were adhered to each other. Each of the obtained samples was subjected to the following test of non-fluidity→fluidity, and then subjected to the following test of fluidity→non-fluidity (return).

<Test of Non-Fluidity→Fluidity>

A portion (A) shown in FIG. 3 was fixed to a table with a cellophane tape, and a 30-cm long vinyl string having a weight of 150 g attached thereto was fixed to a portion (C) with a cellophane tape. A portion (B) was irradiated with light having a wavelength of 365 nm at an irradiation amount of 18 J/cm², and whether or not the cover glass 2 was peeled off from the cover glass 1 was observed and determined according to the following evaluation criteria. The results are shown in Table 2 below.

—Evaluation Criteria for Test of Non-Fluidity→Fluidity—
  ⊙: The cover glass 2 was completely peeled off from the cover glass 1.
  ○: The cover glass 2 and the cover glass 1 were displaced with respect to each other.
  x: The cover glass 2 did not move.

<Test of Fluidity→Non-Fluidity (Return)>

After completion of the test of non-fluidity→fluidity, the following experiment was conducted on a sample in which the cover glass 2 was completely peeled off and a sample in which the cover glass 2 was displaced. For the sample in which the cover glass was displaced, the cover glasses 1 and 2 were peeled off by hand. After 10 minutes from the end of light irradiation in the test of non-fluidity→fluidity (for 10 minutes, left in a natural environment, that is, in a dark room at room temperature), a cover glass 3 (having the same size as those of the cover glasses 1 and 2) was placed so as to cover the sample portion (portion (B)) of the cover glass 1 used in the above-mentioned test, and whether or not the cover glasses 1 and 3 were adhered to each other was observed and determined according to the following evaluation criteria. The results are shown in Table 2 below.

—Evaluation Criteria for Test of Fluidity→Non-Fluidity (Return)—
  ⊙: Did not adhere (non-fluidized)
  ○: Partially adhered (a fluidized state was maintained in some portion)
  x: Adhered (a fluidized state was maintained).

[Evaluation: Fixability Test]

The fixability test was conducted in a normal temperature and normal humidity environment (temperature: 20° C., relative humidity: 50% RH) using the developers of examples and comparative examples obtained as described above. Specifically, a developer was disposed while being slid by a magnetic force between a pair of parallel plate (aluminum) electrodes having a developer on one side and CF paper (basis weight: 80 g/m²) on the other side. The toner was developed at a gap between electrodes of 0.5 mm under conditions of a DC bias and an AC bias so that the toner adhesion amount would be 6 g/m², and a toner layer was formed on the surface of the CF paper and fixed by each of the following fixing devices to produce a printed matter (image formation).

A 1-cm square image of the printed matter was rubbed 20 times with "JK Wiper (registered trademark)" (manufactured by NIPPON PAPER CRECIA CO., LTD.) under a pressure of 30 kPa, and the fixing rate of the image was evaluated. A fixing rate of 60% or more is regarded as acceptable. Herein, the image fixing rate is a numerical value obtained by measuring the densities of the image after printing and the image after rubbing with a reflection densitometer "RD-918" (manufactured by SAKATA INX ENG. CO., LTD.), and dividing the reflection density of the rubbed solid image by the reflection density of the printed solid image, and is expressed in percentage. The results are shown in Table 3 below.

As for the fixing device, the following four types of fixing devices formed by appropriately modifying the device illustrated in FIG. 2 were used.

No. 1: In FIG. 2, the pressure-bonding unit 9 is omitted, the temperature of the heating member 93 is 20° C., the wavelength of ultraviolet light irradiated from the light source 41 is 365 nm (light source: an LED light source having an emission wavelength of 365 nm±10 nm), and the irradiation amount is 11 J/cm².

No. 2: In FIG. 2, the pressure-bonding unit 9 is provided, the temperature of the heating member 93 is 20° C., the temperature of the pressurizing member 91 is 20° C., and the pressure at the time of pressurization is 0.2 MPa. The wavelength and the irradiation amount of the light source 41 are the same as in No. 1.

No. 3: In FIG. 2, the pressure-bonding unit 9 is provided, the temperature of the heating member 93 is 20° C., the temperature of the pressurizing member 91 is 80° C., and the pressure at the time of pressurization is 0.2 MPa. The wavelength and the irradiation amount of the light source 41 are the same as in No. 1.

No. 4: In FIG. 2, the pressure-bonding unit 9 is omitted, the temperature of the heating member 93 is 80° C., and the wavelength and the irradiation amount of the light source 41 are the same as in No. 1.

—Evaluation Criteria for Fixability—
  ⊙: The fixing rate is 85% or more.
  ○: The fixing rate is 80% or more and less than 85%.
  Δ: The fixing rate is 60% or more and less than 80%.
  x: The fixing rate is less than 60%.

[Evaluation of Document Offset Resistance]

Printed matters were produced in a normal temperature and normal humidity environment (temperature: 20° C., relative humidity: 50% RH) using the developers 1 to 19 and the developers of Comparative Examples 1 to 8 obtained as described above. A developer was disposed while being slid by a magnetic force between a pair of parallel plate (aluminum) electrodes having a developer on one side and a sheet as a recording medium (CF paper, basis weight: 80 g/m²) on the other side. The toner was developed at a gap between electrodes of 0.5 mm under conditions of a DC bias and an AC bias so that the toner adhesion amount would be 5 g/m², and a toner layer was formed on the surface of the CF paper and fixed by the fixing device of No. 1 to give 10 printed matters (image formation). The wavelength of ultraviolet light irradiated from irradiation unit 40 was 365 nm (light source: an LED light source having an emission wavelength of 365 nm±10 nm), and the irradiation amount was 12 J/cm².

The 10 output printed matters were then arranged as such on a marble table, and a weight was placed so as to apply a pressure of 19.6 kPa (200 g/cm²) to an overlapped portion. In this state, being left standing in an environment at a temperature of 30° C. and a relative humidity of 60% RH for 3 days, and the superposed printed matters were then separated. In accordance with the criteria shown below, the degrees of image loss on the toner images and offset to a non-image portion on the back of the sheet were evaluated for document offset resistance. The rank 4 or higher was regarded as acceptable. The evaluation results are shown in Table 3 below.

—Evaluation Criteria for Document Offset Resistance—

5: No image loss or image transfer is observed in either the image portion or the non-image portion.

4: There is no image loss in the image portion, but image transfer is slightly observed in the non-image portion on the back of the sheet.

3: There is almost no image loss in the image portion, which is an acceptable level, but image transfer is a little observed in the non-image portion on the back of the sheet.

2: White spots as image loss occur in some areas of the image portion, and transfer to the non-image portion on the back of the sheet is observed in some areas.

1: The fixed image on the image portion is peeled off, the image loss is marked, and evident transfer of the image to the non-image portion on the back of the sheet is observed.

[Color Reproducibility Evaluation]

For the images of examples and comparative examples obtained in the fixability test, color reproducibility was evaluated on the basis of visual evaluation by 10 panelists in accordance with the following evaluation criteria. Specifically, as a comparative sample for evaluation, a toner obtained by removing the photoresponsive compound from the toner of each example was prepared. Using the toner, a developer was produced in the same manner as described above, development was performed in the same manner as in the image formation in the fixability test, and fixation was performed with the following fixing device No. 5.

Fixing device No. 5: In FIG. 2, the pressure-bonding unit 9 is provided, the temperature of the heating member 93 is 20° C., the temperature of the pressurizing member 91 is 150° C., the pressure at the time of pressurization is 0.2 MPa, and light irradiation is not performed.

The comparative samples for evaluation and the samples described in examples were shown in sequence to 10 panelists, and the panelists were asked if the colors of the two images were clearly different. The determination results according to the following evaluation criteria for color reproducibility are shown in Table 3 below.

Evaluation Criteria for Color Reproducibility

⊙: 2 or less panelists answered that the images had clearly different colors.

○: 3 or 4 panelists answered that the images had clearly different colors.

Δ: 5 to 7 panelists answered that the images had clearly different colors.

x: 8 or more panelists answered that the images had clearly different colors.

TABLE 1

| Compound No. | Structure |
|---|---|
| 1 | 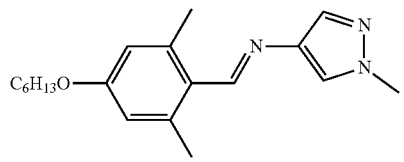 |
| 2 | 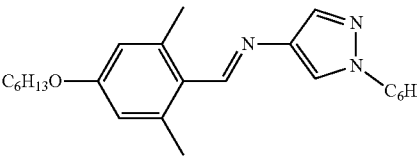 |
| 3 | 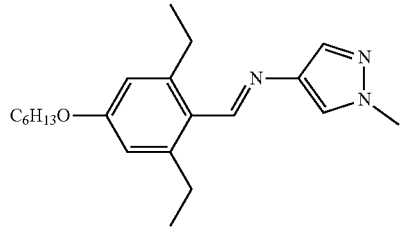 |
| 4 | 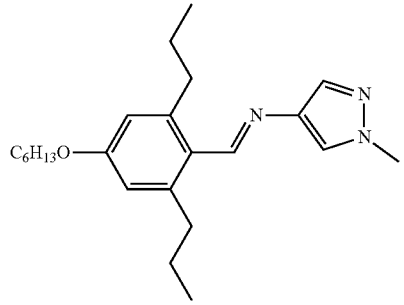 |
| 5 | 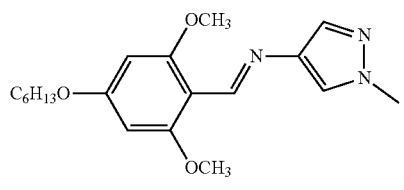 |
| 6 | 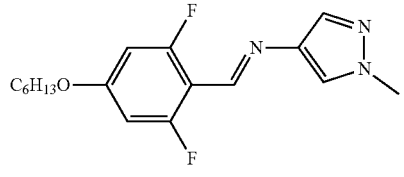 |
| 7 | 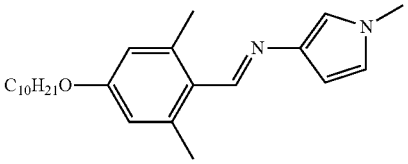 |
| 8 | 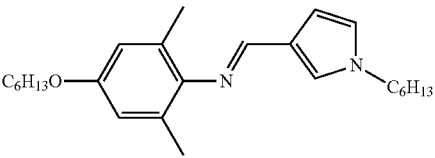 |

TABLE 1-continued

| Compound No. | Structure |
|---|---|
| 9 | 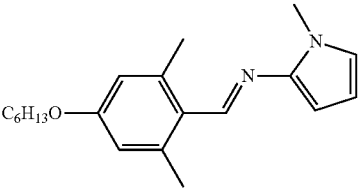 |
| 10 | 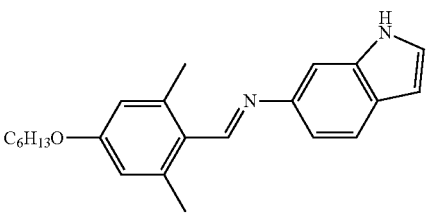 |
| 11 | 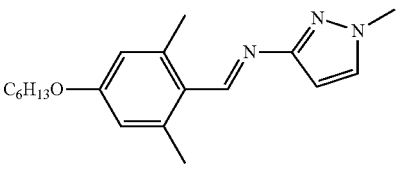 |
| 12 | 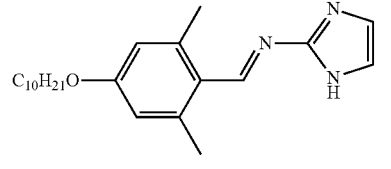 |
| 13 | 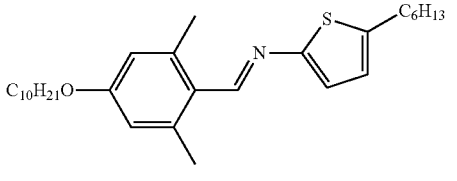 |
| 14 | 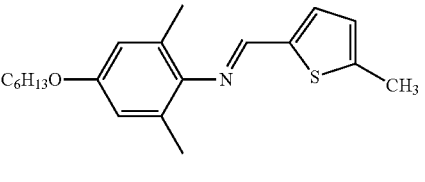 |
| Comparative 1 | 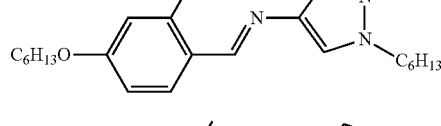 |
| Comparative 2 | 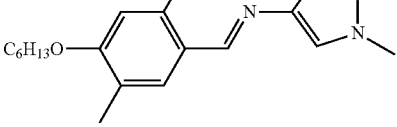 |
| Comparative 3 | 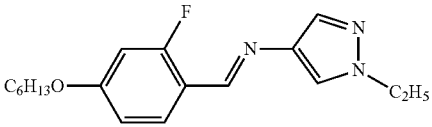 |
| Comparative 4 | 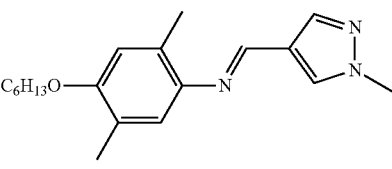 |
| Comparative 5 | |
| Comparative 6 | |
| Comparative 7 | |
| Comparative 8 | Azobenzene compound |

TABLE 2

| Compound No. | Photoresponsive adhesion test | |
|---|---|---|
| | Fluidized | Non-fluidized |
| 1 | ⊙ | ⊙ |
| 2 | ⊙ | ⊙ |
| 3 | ⊙ | ⊙ |
| 4 | ⊙ | ⊙ |
| 5 | ⊙ | ⊙ |
| 6 | ⊙ | ⊙ |
| 7 | ⊙ | ⊙ |
| 8 | ⊙ | ⊙ |
| 9 | ⊙ | ⊙ |
| 10 | ⊙ | ⊙ |
| 11 | ⊙ | ⊙ |
| 12 | ⊙ | ⊙ |
| 13 | ⊙ | ⊙ |
| 14 | ⊙ | ⊙ |
| Comparative 1 | ○ | ⊙ |
| Comparative 2 | ○ | ⊙ |
| Comparative 3 | ○ | ⊙ |
| Comparative 4 | ○ | ⊙ |
| Comparative 5 | ○ | ⊙ |
| Comparative 6 | ○ | ⊙ |
| Comparative 7 | X | — |
| Comparative 8 | ⊙ | X |

TABLE 3

| Example No. | Toner No. | Compound Compound No. | Compound Ratio (mass %) | Binder resin Type | Binder resin Ratio (mass %) | Fixing device No. | Fixability Rank | Fixability Fixing rate (%) | Color reproducibility | Document offset resistance |
|---|---|---|---|---|---|---|---|---|---|---|
| Example 1 | 1 | 1 | 30 | Styrene acrylic resin | 70 | 1 | ⊙ | 89 | ⊙ | 4 |
| Example 2 | 2 | 2 | 30 | Styrene acrylic resin | 70 | 1 | ⊙ | 91 | ⊙ | 5 |
| Example 3 | 3 | 3 | 30 | Styrene acrylic resin | 70 | 1 | ⊙ | 90 | ⊙ | 5 |
| Example 4 | 4 | 4 | 30 | Styrene acrylic resin | 70 | 1 | ⊙ | 90 | ⊙ | 5 |
| Example 5 | 5 | 5 | 30 | Styrene acrylic resin | 70 | 1 | ⊙ | 89 | ⊙ | 4 |
| Example 6 | 6 | 6 | 30 | Styrene acrylic resin | 70 | 1 | ○ | 80 | ⊙ | 4 |
| Example 7 | 7 | 7 | 30 | Styrene acrylic resin | 70 | 1 | ⊙ | 88 | ⊙ | 4 |
| Example 8 | 8 | 8 | 30 | Styrene acrylic resin | 70 | 1 | ○ | 83 | ⊙ | 4 |
| Example 9 | 9 | 9 | 30 | Styrene acrylic resin | 70 | 1 | ⊙ | 87 | ⊙ | 4 |
| Example 10 | 10 | 10 | 30 | Styrene acrylic resin | 70 | 1 | ⊙ | 86 | ⊙ | 4 |
| Example 11 | 11 | 11 | 30 | Styrene acrylic resin | 70 | 1 | ⊙ | 86 | ⊙ | 4 |
| Example 12 | 12 | 12 | 30 | Styrene acrylic resin | 70 | 1 | ⊙ | 85 | ⊙ | 4 |
| Example 13 | 13 | 13 | 30 | Styrene acrylic resin | 70 | 1 | ⊙ | 85 | ⊙ | 4 |
| Example 14 | 14 | 14 | 30 | Styrene acrylic resin | 70 | 1 | ○ | 84 | ⊙ | 4 |
| Comparative Example 1 | Comparative 1 | Comparative 1 | 30 | Styrene acrylic resin | 70 | 1 | Δ | 79 | ⊙ | 3 |
| Comparative Example 2 | Comparative 2 | Comparative 2 | 30 | Styrene acrylic resin | 70 | 1 | Δ | 78 | ⊙ | 3 |
| Comparative Example 3 | Comparative 3 | Comparative 3 | 30 | Styrene acrylic resin | 70 | 1 | Δ | 70 | ⊙ | 3 |
| Comparative Example 4 | Comparative 4 | Comparative 4 | 30 | Styrene acrylic resin | 70 | 1 | Δ | 77 | ⊙ | 3 |
| Comparative Example 5 | Comparative 5 | Comparative 5 | 30 | Styrene acrylic resin | 70 | 1 | Δ | 69 | ⊙ | 3 |
| Comparative Example 6 | Comparative 6 | Comparative 6 | 30 | Styrene acrylic resin | 70 | 1 | Δ | 76 | ⊙ | 3 |
| Comparative Example 7 | Comparative 7 | Comparative 7 | 30 | Styrene acrylic resin | 70 | 1 | X | 58 | ⊙ | 2 |
| Comparative Example 8 | Comparative 8 | Comparative 8 | 30 | Styrene acrylic resin | 70 | 1 | X | 29 | X | 1 |

TABLE 3-continued

| Example No. | Toner No. | Compound No. | Ratio (mass %) | Binder resin Type | Ratio (mass %) | Fixing device No. | Fixability Rank | Fixing rate (%) | Color producibility | Document offset resistance |
|---|---|---|---|---|---|---|---|---|---|---|
| Example 1 | 1 | 1 | 30 | Styrene acrylic resin | 70 | 1 | ⊙ | 89 | ⊙ | 4 |
| Example 15 | 15 | 1 | 10 | Styrene acrylic resin | 90 | 1 | ⊙ | 85 | ⊙ | 4 |
| Example 16 | 16 | 1 | 50 | Styrene acrylic resin | 50 | 1 | ⊙ | 89 | ⊙ | 4 |
| Example 17 | 17 | 1 | 70 | Styrene acrylic resin | 30 | 1 | ⊙ | 89 | ⊙ | 4 |
| Example 18 | 18 | 1 | 90 | Styrene acrylic resin | 10 | 1 | ⊙ | 87 | ⊙ | 4 |
| Example 19 | 19 | 1 | 30 | Polyester resin | 70 | 1 | ⊙ | 88 | ⊙ | 4 |
| Example 20 | 1 | 1 | 30 | Styrene acrylic resin | 70 | 2 | ⊙ | 90 | ⊙ | 5 |
| Example 21 | 1 | 1 | 30 | Styrene acrylic resin | 70 | 3 | ⊙ | 92 | ⊙ | 5 |
| Example 22 | 1 | 1 | 30 | Styrene acrylic resin | 70 | 4 | ⊙ | 93 | ⊙ | 5 |

The "compound" in Table 3 refers to the compound of each example or comparative example. In Table 3, the "ratio" of the compound and the "ratio" of the binder resin are the ratio (mass %) of the compound and the ratio (mass %) of the binder resin, respectively, with respect to the total amount of the compound and the binder resin in the toner.

From Table 2 above, it was found that Compounds 1 to 14 of Examples having a specific structure represented by the general formula (1) were fluidized by light irradiation and reversibly non-fluidized. In addition, it was found that the compounds were more efficiently fluidized as compared to the compounds of Comparative Examples 1 to 6 which did not have the specific structure. The compound of Comparative Example 7 which does not have the specific structure is hardly fluidized by light irradiation. In addition, the azobenzene compound of Comparative Example 8 was not reversibly fluidized after being fluidized.

In addition, as shown in Table 3 above, all the toners containing the compounds produced in the examples were fixed by light irradiation, and exhibited high fixability, high image stability and excellent color reproducibility. In addition, it was found that the toners using the compounds produced in examples had higher fixability and higher image stability as compared to the toners using the compounds of Comparative Examples 1 to 6 which did not have the specific structure. The toner using the polymer prepared in Comparative Example 7 had insufficient fixability and image stability. In addition, it was found that the toner of Comparative Example 8 using an azobenzene derivative had low fixability and image stability, and low color reproducibility.

From comparison between the fixing devices, it was found that when the same toner 1 was used and irradiation with an ultraviolet ray was performed under the same conditions, use of the fixing device No. 2 applying pressure with the pressurizing member or the fixing device No. 3 applying heat and pressure simultaneously with the pressurizing member provided higher fixability than use of the fixing device No. 1 which does not use the pressurizing member (comparison among Examples 1, 20 and 21). In addition, when the same toner 1 was used and irradiation with an ultraviolet ray was performed under the same conditions, use of the fixing device No. 4 applying heat with the heating member 93 provided higher fixability than use of the fixing device No. 1 which does not apply heat during irradiation with an ultraviolet ray (comparison between Examples 1 and 22).

DESCRIPTION OF REFERENCE NUMERALS

1 Photoreceptor
2 Charger
3 Exposure device
4 Developing unit
5 Transfer unit (transfer roller)
7 Sheet conveying system
8 Cleaning unit
9 Pressure-bonding unit
10 Image forming unit
11 Sheet feeder
12 Conveying roller
13 Conveyor belt
14 Sheet ejector
15 Manual sheet feeder
16 Tray
17 Thermo-hygrometer
20 Image processing unit
24 Sheet reversing unit
40 Irradiation unit
41 Light source
71 Image reading device
72 Automatic document feeder
85 Blade
90 Control unit
91, 92 Pressurizing member
93 Heating member
100 Image forming apparatus
d Document
S Recording sheet Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2021-078059, filed on Apr. 30, 2021, is incorporated herein by reference in its entirety.

What is claimed is:

1. A compound represented by the following general formula (1), which is fluidized by light irradiation and reversibly non-fluidized:

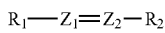

General Formula (1)

wherein $Z_1$ and $Z_2$ are CH or N, and $Z_1 \neq Z_2$;

$R_1$ is an aromatic hydrocarbon group having a substituent $R_a$ selected from the group consisting of an alkyl group, an alkoxy group and a halogen atom at each of two ortho positions with respect to $Z_1$; and $R_2$ is represented by the following formula:

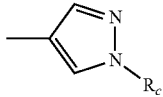

wherein $R_c$ is an alkyl group having 1 to 18 carbon atoms, or an alkoxy group having 1 to 18 carbon atoms.

2. The compound according to claim 1, wherein $R_a$ is an alkyl group having 1 to 5 carbon atoms, an alkoxy group having 1 to 5 carbon atoms, or a halogen atom.

3. The compound according to claim 1, wherein $R_1$ is a phenyl group further having a substituent selected from the group consisting of an alkyl group having 1 to 18 carbon atoms, an alkoxy group having 1 to 18 carbon atoms, a dialkylamino group having 2 to 10 carbon atoms, an acyl group having 2 to 19 carbon atoms, and an alkoxycarbonyl group having 2 to 19 carbon atoms at a para position with respect to $Z_1$.

4. The compound according to claim 1, wherein a wavelength of light in the light irradiation is 280 nm or more and 480 nm or less.

5. A toner comprising the compound set forth in claim 1.

6. The toner according to claim 5, further comprising a binder resin.

7. The toner according to claim 6, wherein the binder resin comprises at least one selected from the group consisting of a styrene acrylic resin and a polyester resin.

8. An image forming method comprising:
 forming a toner image containing the toner set forth in claim 5 on a recording medium; and
 irradiating the toner image with light to soften the toner image.

9. The image forming method according to claim 8, wherein a wavelength of the light is 280 nm or more and 480 nm or less.

10. The image forming method according to claim 8, further comprising pressurizing the toner image.

11. The image forming method according to claim 10, wherein the toner image is further heated in the pressurizing.

12. The image forming method according to claim 8, wherein in the irradiating the toner image with light to soften the toner image, the toner image is heated while being irradiated with light.

13. A photoresponsive adhesive comprising the compound set forth in claim 1.

14. An optical switching material comprising the compound set forth in claim 1.

* * * * *